US006884757B2

(12) United States Patent
Ziemer et al.

(10) Patent No.: US 6,884,757 B2
(45) Date of Patent: Apr. 26, 2005

(54) HERBICIDES COMPRISING BENZOYLCYCLOHEXANEDIONES AND SAFENERS

(75) Inventors: Frank Ziemer, Kriftel (DE); Andreas van Almsick, Karben (DE); Lothar Willms, Hofheim (DE); Thomas Auler, Bad Soden (DE); Hermann Bieringer, Eppstein (DE); Erwin Hacker, Hochheim (DE); Christopher Rosinger, Hofheim (DE)

(73) Assignee: Aventis CropScience GmbH, Frankfurt (DE)

( * ) Notice: Subject to any disclaimer, the term of this patent is extended or adjusted under 35 U.S.C. 154(b) by 0 days.

(21) Appl. No.: 10/126,041

(22) Filed: Apr. 18, 2002

(65) Prior Publication Data

US 2003/0078167 A1 Apr. 24, 2003

(30) Foreign Application Priority Data

Apr. 21, 2001 (DE) .......................................... 101 19 721

(51) Int. Cl.[7] ......................... A01N 25/32; A01N 35/06; A01N 43/80
(52) U.S. Cl. ........................ 504/106; 504/271; 504/348
(58) Field of Search ............................... 504/106, 271, 504/348, 108

(56) References Cited

U.S. PATENT DOCUMENTS

| 5,441,922 A | 8/1995 | Ort et al. | 504/104 |
| 6,376,429 B1 * | 4/2002 | Van Almsick et al. | 504/271 |
| 2002/0123428 A1 * | 9/2002 | Hack et al. | 504/139 |

FOREIGN PATENT DOCUMENTS

| DE | 199 61 465 A1 | 7/2000 |
| EP | 0 551 650 A2 | 7/1993 |
| EP | 0 943 240 | 11/2001 |
| GB | 2 350 298 A | 11/2000 |
| WO | WO 92/19107 | 11/1992 |
| WO | WO 98/27049 | 6/1998 |
| WO | WO 98/34480 | 8/1998 |
| WO | WO 99/66795 | 12/1999 |
| WO | WO 00/00029 | 1/2000 |
| WO | WO 00/21924 | 4/2000 |
| WO | WO 00/30447 | 6/2000 |
| WO | WO 01/07422 | 2/2001 |
| WO | WO 01/17350 A | 3/2001 |

OTHER PUBLICATIONS

Brighton Crop Protection Conference– Weeds–1991, Beraud et al, "A New Herbicide for the Control of Annual Weeds in Maize", vol. 1, pp. 51–56.

Brighton Crop Protection Conference, Weeds—1995, vol. 1, Proceedings of an international conference organized by The British Crop Protection Council held at the Brighton Centre and the Brighton Metropole Hotel, Brighton, England, Nov. 20–23, 1995.

* cited by examiner

Primary Examiner—S. Mark Clardy
(74) Attorney, Agent, or Firm—Frommer, Lawrence & Haug LLP

(57) ABSTRACT

Herbicidal compositions are described that comprise active substances from the group of the benzoylcyclohexanediones and also safeners. These herbicidal compositions are especially suitable for use against weed plants in crop plant cultures.

13 Claims, No Drawings

HERBICIDES COMPRISING BENZOYLCYCLOHEXANEDIONES AND SAFENERS

The invention pertains to the technical field of crop protectants, especially herbicide/antidote combinations (active substance/safener combinations) suitable for use against competing weed plants in crop plant cultures.

Numerous active herbicidal substances are known to be inhibitors of the enzyme p-hydroxyphenylpyruvate dioxygenase (HPPD). For instance, Proc. Br. Crop Prot. Conf. Weeds, 1991, 1, 51; Proc. Br. Crop Prot. Conf. Weeds, 1995, 1, 35 disclose benzoylcyclohexanediones, benzoylpyrazoles, and benzoylisoxazoles of this kind. More recently, further such active substances have been disclosed, for example, in WO 00/21924 and WO 01/07422.

As with many other active herbicidal substances, these HPPD inhibitors too are not always sufficiently compatible with (i.e., lack sufficient selectivity for) certain important crop plants, such as corn, rice or cereals, whereby imposing narrow limitations on their use. In some crops, therefore, they cannot be used, or can be used only at such low application rates that the desired broad herbicidal activity toward weed plants is not ensured. More particularly, many of these herbicides lack complete selectivity for weed plants in corn, rice, cereals, sugar cane, and certain other crops.

A known means for overcoming these disadvantages is to use active herbicidal substances in combination with a substance known as a safener or antidote. EP-A 0 943 240, WO 99/66795, and WO 00/30447, for example, describe various combinations of certain HPPD inhibitors with safeners.

A safener is a compound which eliminates or lessens the phytotoxic properties of a herbicide toward crop plants without substantially reducing the herbicidal action toward weed plants.

Identifying a safener for a particular group of herbicides is still a difficult task, since the precise mechanisms by which a safener lessens the noxious effect of herbicides are unknown. Consequently, the fact that a compound acts as safener in combination with one particular herbicide does not permit conclusions as to the safener action of such a compound with other groups of herbicides. In the use of safeners to protect crop plants against herbicide damage, it has been found that the safeners in many cases may still have certain disadvantages. These include the following:

the safener lessens the action of the herbicides toward the weed plants;
the crop plant protecting properties are inadequate;
with a given herbicide, the spectrum of crop plants in which the safener/herbicide combination is to be used is too small;
a sufficiently large number of herbicides cannot be combined with a given safener.

It is an object of the present invention to provide further combinations of herbicides from the group of the HPPD inhibitors with safeners that are suitable for raising the selectivity of these herbicides with respect to important crop plants.

Novel combinations have now been found of certain herbicides from the group of the HPPD inhibitors which carry selected substituents in position 3 of the benzoyl moiety with numerous other compounds which raise the selectivity of these herbicides with respect to important crop plants.

The invention accordingly provides a herbicidally active composition comprising

A) a herbicidally effective amount of one or more compounds of the formula (I)

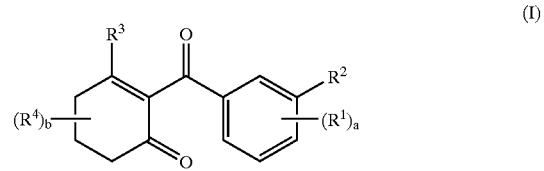

(I)

in which the symbols and indices have the following definitions:

$R^1$ is nitro, amino, halogen, cyano, $(C_1–C_4)$-alkyl, $(C_2–C_4)$-alkenyl, $(C_2–C_4)$-alkynyl, $(C_1–C_4)$-haloalkyl, $(C_2–C_4)$-haloalkenyl, $(C_2–C_4)$-haloalkynyl, $(C_1–C_4)$-haloalkoxy, $(C_1–C_4)$-haloalkylthio, $(C_1–C_4)$-alkoxycarbonyl, $(C_1–C_4)$-alkylsulfonyl, $(C_1–C_4)$-alkylsulfinyl, $(C_1–C_4)$-alkylthio, $(C_1–C_4)$-alkoxy, $(C_1–C_4)$-alkoxy-$(C_1–C_4)$-alkoxy, $(C_1–C_4)$-alkylcarbonyl, $(C_1–C_4)$-alkylaminosulfonyl, $(C_1–C_4)$-dialkylaminosulfonyl, $(C_1–C_4)$-alkylcarbamoyl, $(C_1–C_4)$-dialkylcarbamoyl, $(C_1–C_4)$-alkoxy-$(C_1–C_4)$-alkyl, $(C_1–C_4)$-alkylamino or $(C_1–C_4)$-dialkylamino;

$R^2$ is $(C_1–C_4)$-haloalkoxy-$(C_1–C_4)$-alkyl, $(C_1–C_4)$-alkoxy-$(C_1–C_4)$-alkoxy-$(C_1–C_4)$-alkyl, $(C_3–C_6)$-cycloalkoxy-$(C_1–C_4)$-alkyl, $(C_3–C_6)$-cycloalkyl-$(C_1–C_4)$-alkoxy, tetrahydrofuran-2-yl-methoxy-$(C_1–C_4)$-alkyl, tetrahydrofuran-3-yl-methoxy-$(C_1–C_4)$-alkyl or a heterocyclic radical from the group consisting of isoxazol-3-yl and 4,5-dihydroisoxazol-3-yl which is substituted by a radical from the group consisting of cyanomethyl, ethoxymethyl and methoxymethyl;

$R^3$ is $OR^5$, cyano, halogen, cyanato, thiocyanato, $(C_1–C_4)$-alkylthio, $(C_1–C_4)$-alkylsulfinyl, $(C_1–C_4)$-alkylsulfonyl, $(C_2–C_4)$-alkenylthio, $(C_2–C_4)$-alkenylsulfinyl, $(C_2–C_4)$-alkenylsulfonyl, $(C_2–C_4)$-alkynylthio, $(C_2–C_4)$-alkynylsulfinyl, $(C_2–C_4)$-alkynylsulfonyl, $(C_1–C_4)$-haloalkylthio, $(C_2–C_4)$-haloalkenylthio, $(C_2–C_4)$-haloalkynylthio, $(C_1–C_4)$-haloalkylsulfinyl, $(C_2–C_4)$-haloalkenylsulfinyl, $(C_2–C_4)$-haloalkynylsulfinyl, $(C_1–C_4)$-haloalkylsulfonyl, $(C_2–C_4)$-haloalkenylsulfonyl or $(C_2–C_4)$-haloalkynylsulfonyl;

$R^4$ is $(C_1–C_4)$-alkyl;

$R^5$ is hydrogen, $(C_1–C_4)$-alkyl, $(C_1–C_4)$-haloalkyl or $(C_1–C_4)$-alkoxy-$(C_1–C_4)$-alkyl;

a is 0, 1, 2 or 3;
b is 0, 1 or 2; and

B) an antidote-active amount of one or more compounds from groups a) to e):
a) compounds of the formulae (II) to (IV),

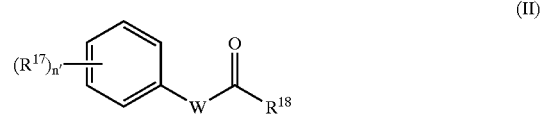

(II)

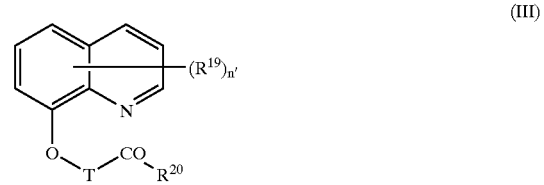

(III)

-continued

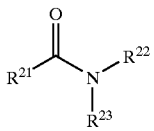
(IV)

in which the symbols and indices have the following definitions:

n' is a natural number from 0 to 5, preferably from 0 to 3;

T is a ($C_1$- or $C_2$-)-alkanediyl chain which is unsubstituted or substituted by one or two ($C_1$–$C_4$)-alkyl radicals or by [($C_1$–$C_3$)-alkoxy]carbonyl;

W is a radical from the group (W1) to (W4),

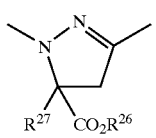
(W1)

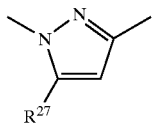
(W2)

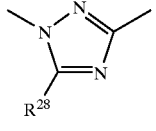
(W3)

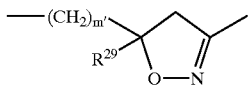
(W4)

m' is 0 or 1;

$R^{17}$ and $R^{19}$ are identical or different and are halogen, ($C_1$–$C_4$)-alkyl, ($C_1$–$C_4$)-alkoxy, nitro or ($C_1$–$C_4$)-haloalkyl;

$R^{18}$ and $R^{20}$ are identical or different and are $OR^{24}$, $SR^{24}$ or $NR^{24}R^{25}$ or a saturated or unsaturated 3- to 7-membered heterocycle containing at least one nitrogen atom and up to 3 heteroatoms which is bonded by the nitrogen atom to the carbonyl group in (II) or (III) and is unsubstituted or substituted by radicals from the group consisting of ($C_1$–$C_4$)-alkyl, ($C_1$–$C_4$)-alkoxy and unsubstituted or substituted phenyl, preferably a radical of the formula $OR^{24}$, $NHR^{25}$ or $N(CH_3)_2$, in particular of the formula $OR^{24}$;

$R^{24}$ is hydrogen or an unsubstituted or substituted aliphatic hydrocarbon radical, preferably having a total of from 1 to 18 carbon atoms;

$R^{25}$ is hydrogen, ($C_1$–$C_6$)-alkyl, ($C_1$–$C_6$)-alkoxy or substituted or unsubstituted phenyl;

$R^{26}$ is hydrogen, ($C_1$–$C_8$)-alkyl, ($C_1$–$C_8$)-haloalkyl, ($C_1$–$C_4$)-alkoxy-($C_1$–$C_4$)-alkyl, ($C_1$–$C_6$)-hydroxyalkyl, ($C_3$–$C_{12}$)-cycloalkyl or tri-($C_1$–$C_4$)-alkylsilyl;

$R^{27}$, $R^{28}$ and $R^{29}$ are identical or different and are hydrogen, ($C_1$–$C_8$)-alkyl, ($C_1$–$C_6$)-haloalkyl, ($C_3$–$C_{12}$)-cycloalkyl or substituted or unsubstituted phenyl;

$R^{21}$ is ($C_1$–$C_4$)-alkyl, ($C_1$–$C_4$)-haloalkyl, ($C_2$–$C_4$)-alkenyl, ($C_2$–$C_4$)-haloalkenyl, ($C_3$–$C_7$)-cycloalkyl, preferably dichloromethyl;

$R^{22}$, $R^{23}$ are identical or different and are hydrogen, ($C_1$–$C_4$)-alkyl, ($C_2$–$C_4$)-alkenyl, ($C_2$–$C_4$)-alkynyl, ($C_1$–$C_4$)-haloalkyl, ($C_2$–$C_4$)-haloalkenyl, ($C_1$–$C_4$)-alkylcarbamoyl-($C_1$–$C_4$)-alkyl, ($C_2$–$C_4$)-alkenylcarbamoyl-($C_1$–$C_4$)-alkyl, ($C_1$–$C_4$)-alkoxy-($C_1$–$C_4$)-alkyl, dioxolanyl-($C_1$–$C_4$)-alkyl, thiazolyl, furyl, furylalkyl, thienyl, piperidyl, substituted or unsubstituted phenyl, or $R^{22}$ and $R^{23}$ together form a substituted or unsubstituted heterocyclic ring, preferably an oxazolidine, thiazolidine, piperidine, morpholine, hexahydropyrimidine or benzoxazine ring;

b) one or more compounds from the following group:

1,8-naphthalic anhydride, methyl diphenylmethoxyacetate, cyanomethoxyimino(phenyl)acetonitrile (cyometrinile), 1,3-dioxolan-2-ylmethoxyimino(phenyl)acetonitrile (oxabetrinil), 4'-chloro-2,2,2-trifluoroacetophenone O-1,3-dioxolan-2-ylmethyl oxime (fluxofenim), 4,6-dichloro-2-phenylpyrimidine (fenclorim), benzyl 2-chloro-4-trifluoromethyl-1,3-thiazole-5-carboxylate (flurazole), 2-dichloromethyl-2-methyl-1,3-dioxolane (MG-191), N-(4-methylphenyl)-N'-(1-methyl-1-phenylethyl)urea (dymron), 1-[4-(N-2-methoxybenzoylsulfamoyl)phenyl]-3-methylurea, 1-[4-(N-2-methoxybenzoylsulfamoyl)phenyl]-3,3-dimethylurea, 1-[4-(N-4,5-dimethylbenzoylsulfamoyl)phenyl]-3-methylurea, 1-[4-(N-naphthoylsulfamoyl)phenyl]-3,3-dimethylurea, (2,4-dichlorophenoxy)acetic acid (2,4-D), (4-chlorophenoxy)acetic acid, (R,S)-2-(4-chloro-o-tolyloxy)propionic acid (mecoprop), 4-(2,4-dichlorophenoxy)butyric acid (2,4-DB), (4-chloro-o-tolyloxy)acetic acid (MCPA), 4-(4-chloro-o-tolyloxy)butyric acid, 4-(4-chlorophenoxy)butyric acid, 3,6-dichloro-2-methoxybenzoic acid (dicamba), 1-(ethoxycarbonyl)ethyl 3,6-dichloro-2-methoxybenzoate (lactidichlor)

and their salts and esters, preferably ($C_1$–$C_8$);

c) N-acylsulfonamides of the formula (V) and their salts,

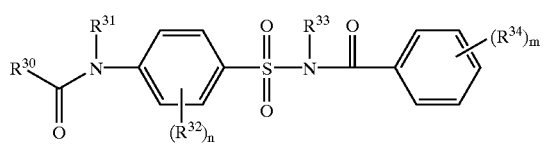
(V)

in which $R^{30}$ is hydrogen, a carbon-containing radical such as a hydrocarbon radical, a hydrocarbon-oxy radical, a hydrocarbon-amino radical, a hydrocarbon-thio radical or a heterocyclyl radical, each of the 4 last-mentioned radicals being unsubstituted or being substituted by one or more identical or different radicals selected from the group consisting of halogen, cyano, nitro, amino, hydroxyl, carboxyl, formyl, carboxamide, sulfonamide and radicals of the formula -$Z^a$-$R^a$, each hydrocarbon moiety preferably having 1 to 20 carbon atoms and a carbon-containing radical $R^{30}$ inclusive of substituents preferably having 1 to 30 carbon atoms;

$R^{31}$ is hydrogen or $(C_1-C_4)$-alkyl, preferably hydrogen, or $R^{30}$ and $R^{31}$ together with the group of the formula —CO—N— are the residue of a 3- to 8-membered saturated or unsaturated ring;

$R^{32}$ is identical or different and is halogen, cyano, nitro, amino, hydroxyl, carboxyl, formyl, $CONH_2$, $SO_2NH_2$ or a radical of the formula $-Z^b-R^b$;

$R^{33}$ s hydrogen or $(C_1-C_4)$-alkyl, preferably hydrogen;

$R^{34}$ is identical or different and is halogen, cyano, nitro, amino, hydroxyl, carboxyl, CHO, $CONH_2$, $SO_2NH_2$ or a radical of the formula $-Z^c-R^c$;

$R^a$ is a hydrocarbon radical or a heterocyclyl radical, each of the two last-mentioned radicals being unsubstituted or substituted by one or more identical or different radicals selected from the group consisting of halogen, cyano, nitro, amino, hydroxyl, mono- and di-$[(C_1-C_4)$-alkyl]amino, or an alkyl radical in which a plurality, preferably 2 or 3, non-adjacent $CH_2$ groups are in each case replaced by one oxygen atom;

$R^b, R^c$ are identical or different and are a hydrocarbon radical or a heterocyclyl radical, each of the two last-mentioned radicals being unsubstituted or substituted by one or more identical or different radicals selected from the group consisting of halogen, cyano, nitro, amino, hydroxyl, phosphoryl, halo-$(C_1-C_4)$-alkoxy, mono- and di-$[(C_1-C_4)$-alkyl]amino, or an alkyl radical in which a plurality, preferably 2 or 3, non-adjacent $CH_2$ groups are replaced in each case by one oxygen atom;

$Z^a$ is a divalent group of the formula —O—, —S—, —CO—, —CS—, —CO—O—, —CO—S—, —O—CO—, —S—CO—, —SO—, —SO_2—, —NR*—, —CO—NR*—, —NR*—CO—, —SO_2—NR*— or —NR*—SO_2—, the bond given on the right-hand side of each of the divalent groups being the bond to the radical $R^a$, and the radicals R* in the 5 last-mentioned radicals independently of each other being in each case H, $(C_1-C_4)$-alkyl or halo-$(C_1-C_4)$-alkyl;

$Z^b, Z^c$ independently of one another are a direct bond or a divalent group of the formula —O—, —S—, —CO—, —CS—, —CO—O—, —CO—S—, —O—CO—, —S—CO—, —SO, $SO_2$—, —NR*—, —$SO_2$—NR*—, —NR*—$SO_2$—, —CO—NR*— or —NR*—CO—, the bond given on the right-hand side of each of the divalent groups being the bond is linked to the radical $R^b$ or $R^c$ and the radicals R* in the 5 last-mentioned radicals independently of one another are in each case H, $(C_1-C_4)$-alkyl or halo-$(C_1-C_4)$-alkyl;

n is an integer from 0 to 4, preferably 0, 1 or 2, in particular 0 or 1, and m is an integer from 0 to 5, preferably 0, 1, 2 or 3, in particular 0, 1 or 2;

d) acylsulfamoylbenzamides of the formula (VI), optionally also in salt form,

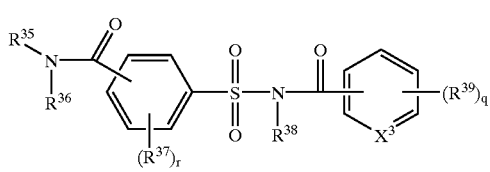

(VI)

in which $X^3$ is CH or N;

$R^{35}$ is hydrogen, heterocyclyl or a hydrocarbon radical, the two last-mentioned radicals optionally being substituted by one or more identical or different radicals selected from the group consisting of halogen, cyano, nitro, amino, hydroxyl, carboxyl, CHO, $CONH_2$, $SO_2NH_2$ and $Z^a-R^a$;

$R^{36}$ is hydrogen, hydroxyl, $(C_1-C_6)$-alkyl, $(C_2-C_6)$-alkenyl, $(C_2-C_6)$-alkynyl, $(C_1-C_6)$-alkoxy, $(C_2-C_6)$-alkenyloxy, the five last-mentioned radicals optionally being substituted by one or more identical or different radicals selected from the group consisting of halogen, hydroxyl, $(C_1-C_4)$-alkyl, $(C_1-C_4)$-alkoxy and $(C_1-C_4)$-alkylthio, or $R^{35}$ and $R^{36}$ together with the nitrogen atom to which they are attached are a 3- to 8-membered saturated or unsaturated ring;

$R^{37}$ is halogen, cyano, nitro, amino, hydroxyl, carboxyl, CHO, $CONH_2$, $SO_2NH_2$ or $Z^b-R^b$;

$R^{38}$ is hydrogen, $(C_1-C_4)$-alkyl, $(C_2-C_4)$-alkenyl or $(C_2-C_4)$-alkynyl;

$R^{39}$ is halogen, cyano, nitro, amino, hydroxyl, carboxyl, phosphoryl, CHO, $CONH_2$, $SO_2NH_2$ or $Z^c-R^c$;

$R^a$ is a $(C_2-C_{20})$-alkyl radical whose carbon chain is interrupted once or more than once by oxygen atoms, or is heterocyclyl or a hydrocarbon radical, the two last-mentioned radicals optionally being substituted by one or more identical or different radicals selected from the group consisting of halogen, cyano, nitro, amino, hydroxyl, mono- and di-$[(C_1-C_4)$-alkyl]amino;

$R^b, R^c$ are identical or different and are a $(C_2-C_{20})$-alkyl radical whose carbon chain is interrupted once or more than once by oxygen atoms, or a heterocyclyl or a hydrocarbon radical, the two last-mentioned radicals optionally being substituted by one or more identical or different radicals selected from the group consisting of halogen, cyano, nitro, amino, hydroxyl, phosphoryl, $(C_1-C_4)$-haloalkoxy, mono- and di-$[(C_1-C_4)$-alkyl]amino;

$Z^a$ is a divalent unit selected from the group consisting of O, S, CO, CS, C(O)O, C(O)S, SO, $SO_2$, $NR^d$, $C(O)NR^d$ or $SO_2NR^d$;

$Z^b, Z^c$ are identical or different and are a direct bond or a divalent unit selected from the group consisting of O, S, CO, CS, C(O)O, C(O)S, SO, $SO_2$, $NR^d$, $SO_2NR^d$ or $C(O)NR^d$;

$R^d$ is hydrogen, $(C_1-C_4)$-alkyl or $(C_1-C_4)$-haloalkyl;

r is an integer from 0 to 4, and q in the event that $X^3$ is CH, is an integer from 0 to 5 and, in the event that X is N, is an integer from 0 to 4;

e) compounds of the formula (VII),

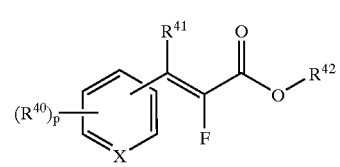

(VII)

in which the symbols and indices have the following definitions:

X is CH or N, p in the event that X=N, is an integer from 0 to 2 and, in the event that X=CH, is an integer from 0 to 3;

$R^{40}$ is halogen, $(C_1-C_4)$-alkyl, $(C_1-C_4)$-haloalkyl, $(C_1-C_4)$-alkoxy, $(C_1-C_4)$-haloalkoxy, nitro, $(C_1-C_4)$-alkylthio, $(C_1-C_4)$-alkylsulfonyl, $(C_1-C_4)$-alkoxycarbonyl, phenyl or phenoxy, the two last-mentioned radicals being unsubstituted or substituted by one or more, preferably up to three, identical or different radicals from the group consisting of halogen, $(C_1-C_4)$-alkyl, $(C_1-C_4)$-haloalkyl, $(C_1-C_4)$-alkoxy, halo-$(C_1-C_4)$-alkoxy, nitro and cyano;

$R^{41}$ is hydrogen or $(C_1-C_4)$-alkyl, and $R^{42}$ is hydrogen, $(C_1-C_8)$-alkyl, $(C_3-C_6)$-cycloalkyl, $(C_2-C_6)$-alkenyl, $(C_2-C_6)$-alkynyl or aryl, each of the aforementioned carbon-containing radicals being unsubstituted or substituted by one or more, preferably up to three, identical or different radicals from the group consisting of halogen, nitro, cyano, hydroxyl, $(C_1-C_8)$-alkoxy, in which one or more, preferably up to three, $CH_2$ groups may be replaced by oxygen, $(C_1-C_4)$-alkylthio, $(C_1-C_4)$-alkylsulfonyl, $(C_3-C_6)$-cycloalkyl, $(C_2-C_4)$-alkenyloxy and $(C_2-C_4)$-alkynyloxy, inclusive of the stereoisomers and the agriculturally customary salts.

A herbicidally effective amount is, for the purposes of the invention, an amount of one or more herbicides which is capable of adversely affecting plant growth.

An antidote-active amount is, for the purposes of the invention, an amount of one or more safeners which is capable of at least partially countering the phytotoxic effect of a herbicide or herbicide mixture on a crop plant.

Unless otherwise defined individually, the following definitions generally apply to the radicals in the formulae (I) to (VIII) and subsequent formulae.

The radicals alkyl, alkoxy, haloalkyl, haloalkoxy, alkylamino and alkylthio and the corresponding unsaturated and/or substituted radicals can be in each case straight-chain or branched in the carbon skeleton. Alkyl radicals, also the composite meanings such as alkoxy, haloalkyl and the like, preferably have 1 to 4 carbon atoms and are, for example, methyl, ethyl, n- or i-propyl or n-, i-, t- or 2-butyl. Alkenyl and alkynyl radicals have the meanings of the unsaturated radicals which are possible and which correspond to the alkyl radicals; alkenyl is, for example, allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl. Alkynyl is, for example, propargyl, but-2-yn-1-yl, but-3-yn-1-yl, 1-methylbut-3-yn-1-yl. "$(C_1-C_4)$-Alkyl" is the abbreviation for alkyl having 1 to 4 carbon atoms; the same applies analogously to other general definitions of radicals, where the ranges of the possible number of carbon atoms are indicated in brackets.

Cycloalkyl is, preferably, a cyclic alkyl radical having 3 to 8, preferably 3 to 7, especially preferably 3 to 6, carbon atoms, for example cyclopropyl, cyclobutyl, cyclopentyl and cyclohexyl. Cycloalkenyl and cycloalkynyl denote corresponding unsaturated compounds.

Halogen is fluorine, chlorine, bromine or iodine. Haloalkyl, haloalkenyl and haloalkynyl are alkyl, alkenyl or alkynyl which are partially or fully substituted by halogen, preferably by fluorine, chlorine and/or bromine, in particular by fluorine or chlorine, for example $CF_3$, $CHF_2$, $CH_2F$, $CF_2CF_3$, $CH_2FCClFM$, $CCl_3$, $CHCl_2$, $CH_2CH_2Cl$. Haloalkoxy is, for example, $OCF_3$, $OCHF_2$, $OCH_2F$, $OCF_2CF_3$, $OCH_2CF_3$ and $OCH_2CH_2Cl$. This also applies analogously to other halogen-substituted radicals.

An aliphatic hydrocarbon radical is generally a straight-chain or branched saturated or unsaturated hydrocarbon radical, preferably having 1 to 18, especially preferably 1 to 12, carbon atoms, for example alkyl, alkenyl or alkynyl. Aryl is generally a mono-, bi- or polycyclic aromatic system having preferably 6 to 14 carbon atoms, for example phenyl, naphthyl, pentalenyltetrahydronaphthyl, indenyl, indanyl and fluorenyl, especially preferably phenyl. Aliphatic hydrocarbon radical preferably means alkyl, alkenyl or alkynyl having up to 12 carbon atoms; the same applies analogously to an aliphatic hydrocarbon radical in a hydrocarbon-oxy radical.

Heterocyclic ring, heterocyclic radical or heterocyclyl is a mono-, bi- or polycyclic ring system which is saturated, unsaturated and/or aromatic and contains one or more, preferably 1 to 4, heteroatoms, preferably selected from the group consisting of N, S and O. Preferred are saturated heterocycles having 3 to 7 ring atoms and one or two heteroatoms selected from the group consisting of N, O and S, chalcogens not being adjacent. Especially preferred are monocyclic rings having 3 to 7 ring atoms and a heteroatom selected from the group consisting of N, O and S, and also morpholine, dioxolane, piperazine, imidazoline and oxazolidine. Very especially preferred saturated heterocycles are oxirane, pyrrolidone, morpholine and tetrahydrofuran. Also preferred are partially unsaturated heterocycles having 5 to 7 ring atoms and one or two heteroatoms selected from the group consisting of N, O and S. Especially preferred are partially unsaturated heterocycles having 5 to 6 ring atoms and one heteroatom selected from the group consisting of N, O and S. Very especially preferred partially unsaturated heterocycles are pyrazoline, imidazoline and isoxazoline. Equally preferred are mono- or bicyclic aromatic heterocycles having 5 to 6 ring atoms which contain one to four heteroatoms selected from the group consisting of N, O, S, chalcogens not being adjacent. Especially preferred are monocyclic aromatic heterocycles having 5 to 6 ring atoms which contain a heteroatom selected from the group consisting of N, O and S, and also pyrimidine, pyrazine, pyridazine, oxazole, thiazole, thiadiazole, oxadiazole, pyrazole, triazole and isoxazole. Very especially preferred are pyrazole, thiazole, triazole and furan.

Substituted radicals, such as substituted hydrocarbon radicals, for example substituted alkyl, alkenyl, alkynyl, aryl, phenyl and arylalkyl such as benzyl, or substituted heterocyclyl or heteroaryl, are a substituted radical which is derived from the unsubstituted parent structure, the substituents being, by preference, one or more, preferably 1, 2 or 3, in the case of Cl and F also up to the maximum possible number of, radicals selected from the group consisting of halogen, alkoxy, haloalkoxy, alkylthio, hydroxyl, amino, nitro, carboxyl, cyano, azido, alkoxycarbonyl, alkylcarbonyl, formyl, carbamoyl, mono- and dialkylaminocarbonyl, substituted amino such as acylamino, mono- and dialkylamino and alkylsulfinyl, haloalkylsulfinyl, alkylsulfonyl, haloalkylsulfonyl and, in the case of cyclic radicals, also alkyl and haloalkyl and the unsaturated aliphatic radicals which correspond to the abovementioned saturated hydrocarbon-containing substituents, preferably alkenyl, alkynyl, alkenyloxy and alkynyloxy. In the case of radicals having carbon atoms, those having 1 to 4 carbon atoms, in particular 1 or 2 carbon atoms, are preferred. As a rule, preferred radicals are those selected from the group consisting of halogen, for example fluorine or chlorine, $(C_1-C_4)$-alkyl, preferably methyl or ethyl, $(C_1-C_4)$-haloalkyl, preferably trifluoromethyl, $(C_1-C_4)$-alkoxy, preferably methoxy or ethoxy, $(C_1-C_4)$-haloalkoxy, nitro and cyano. Especially preferred in this context are the substituents methyl, methoxy and chlorine.

Mono- or disubstituted amino is a chemically stable radical selected from the group of the substituted amino radicals which are N-substituted by, for example, one or two identical or different radicals selected from the group consisting of alkyl, alkoxy, acyl and aryl; preferably monoalkylamino, dialkylamino, acylamino, arylamino, N-alkyl-N-arylamino and N-heterocycles. Preferred in this context are alkyl radicals having 1 to 4 carbon atoms. By preference, aryl is phenyl or substituted phenyl. By preference, substituted aryl is substituted phenyl. The definition given further below applies to acyl, preferably $(C_1-C_4)$-alkanoyl. This also applies analogously to substituted hydroxylamino or hydrazino.

By preference, optionally substituted phenyl is phenyl which is unsubstituted or mono- or polysubstituted, preferably up to trisubstituted, in the case of halogen such as Cl and F also up to pentasubstituted, by identical or different radicals selected from the group consisting of halogen, $(C_1-C_4)$-alkyl, $(C_1-C_4)$-alkoxy, $(C_1-C_4)$-haloalkyl, $(C_1-C_4)$-haloalkoxy and nitro, for example o-, m- and p-tolyl, dimethylphenyls, 2-, 3- and 4-chlorophenyl, 2-, 3- and 4-trifluoro- and -trichlorophenyl, 2,4-, 3,5-, 2,5- and 2,3-dichlorophenyl, o-, m- and p-methoxyphenyl.

An acyl radical is the radical of an organic acid having by preference up to 6 carbon atoms, for example the radical of a carboxylic acid and radicals of acids derived therefrom, such as thiocarboxylic acid, optionally N-substituted iminocarboxylic acids, or the radical of carbonic monoesters, optionally N-substituted carbamic acids, sulfonic acids, sulfinic acids, phosphonic acids, phosphinic acids. Acyl is, for example, formyl, alkylcarbonyl such as $(C_1-C_4$-alkyl) carbonyl, phenylcarbonyl, it being possible for the phenyl ring to be substituted, for example as indicated above for phenyl, or alkyloxycarbonyl, phenyloxycarbonyl, benzyloxycarbonyl, alkylsulfonyl, alkylsulfinyl or N-alkyl-1-iminoalkyl.

All stereoisomers which show the same topological linkage of the atoms, and their mixtures, also fall under the formulae (I) to (VIII). Such compounds contain one or more asymmetric carbon atoms or else double bonds which are not indicated specifically in the general formulae. The stereoisomers which are possible which are defined by their specific spatial form, such as enantiomers, diastereomers, Z- and E-isomers, can be obtained from mixtures of the stereoisomers by customary methods or else be prepared by stereoselective reactions in combination with the use of stereochemically pure starting materials.

Herbicidally active substances which are suitable in accordance with the invention are those compounds of the formula (I) which, on their own, cannot be used, or not optimally used, in crops of useful plants such as cereal crops, rice or corn because they are too harmful to the crop plants.

Herbicides of the formula (I) are known, for example, from WO-A 00/21924 and WO-A 01/7422.

The cited publications contain extensive data on preparation processes and starting materials. These publications are referred to exclusively and are considered by such reference to be part of this description.

The compounds of the formula (II) are known, for example, from EP-A-0 333 131 (ZA-89/1960), EP-A-0 269 806 (U.S. Pat. No. 4,891,057), EP-A-0 346 620 (AU-A-89/34951), EP-A-0 174 562, EP-A-0 346 620 (WO-A-91/08 202), WO-A-91/07 874 or WO-A 95/07 897 (ZA 94/7120) and the literature cited therein or can be prepared by or analogously to the processes described therein. The compounds of the formula (III) are known from EP-A-0 086 750, EP-A-0 94349 (U.S. Pat. No. 4,902,340), EP-A-0 191736 (U.S. Pat. No. 4,881,966) and EP-A-0 492 366 and the literature cited therein or can be prepared by or analogously to the processes described therein. Furthermore, some compounds are described in EP-A-0 582 198. The compounds of the formula (II) are known from a large number of patent applications, for example U.S. Pat. No. 4,021,224 and U.S. Pat. No. 4,021,229. Moreover, compounds of group (b) are known from CN-A-87/102 789, EP-A-0 365 484 and from "The Pesticide Manual", The British Crop Protection Council and the Royal Society of Chemistry, 11th edition, Famham 1997. The compounds of group (c) are described in WO-A-97/45016, those of group (d) in German Patent Application 197 42 951.3 and those of group (e) in WO-A 98/13 361.

The publications cited contain detailed information on preparation processes and starting materials. These publications are referred to explicitly and are considered by such reference to be part of this description.

For the purpose of the present specification, the terms "herbicidal compositions" and "herbicide/safener combinations" are to be understood as being synonymous.

Preference is given to herbicidal compositions comprising compounds of the formula (I) wherein the symbols and indices have the following definitions:

$R^1$ is nitro, cyano, chlorine, fluorine, methyl, trifluoromethyl, methylsulfonyl or ethylsulfonyl;

$R^2$ is pentafluoroethoxymethyl, 2,2-difluoroethoxymethyl, 2,2,2-trifluoroethoxymethyl, 2,2,3,3-tetrafluoropropoxymethyl, cyclopentyloxymethyl, cyclohexyloxymethyl, cyclopropyloxy, tetrahydrofuran-2-ylmethoxymethyl, methoxyethoxyethoxymethyl, or 4,5-dihydroisoxazol-3-yl substituted by a radical from the group consisting of cyanomethyl, ethoxymethyl and methoxymethyl;

$R^3$ is $OR^5$;

$R^5$ is hydrogen;

a is 2;

b is 0, and in which the two radicals $R^1$ are in positions 2 and 4 of the phenyl ring.

Preferred herbicidal compositions are those which comprise safeners of the formula (II) and/or (III) wherein the symbols and indices have the following definitions:

$R^{24}$ is hydrogen, $(C_1-C_{18})$-alkyl, $(C_3-C_{12})$-cycloalkyl, $(C_2-C_8)$-alkenyl and $(C_2-C_{18})$-alkynyl, where the carbon-containing groups can be substituted by one or more, preferably up to three, radicals $R^{50}$;

$R^{50}$ is identical or different and is halogen, hydroxyl, $(C_1-C_8)$-alkoxy, $(C_1-C_8)$-alkylthio, $(C_2-C_8)$-alkenylthio, $(C_2-C_8)$-alkynylthio, $(C_2-C_8)$-alkenyloxy, $(C_2-C_8)$-alkynyloxy, $(C_3-C_7)$-cycloalkyl, $(C_3-C_7)$-cycloalkoxy, cyano, mono- and di-$(C_1-C_4)$-alkylamino, carboxyl, $(C_1-C_8)$-alkoxycarbonyl, $(C_2-C_8)$-alkenyloxycarbonyl, $(C_1-C_8)$-alkylthiocarbonyl, $(C_2-C_8)$-alkynyloxycarbonyl, $(C_1-C_8)$-alkylcarbonyl, $(C_2-C_8)$-alkenylcarbonyl, $(C_2-C_8)$-alkynylcarbonyl, 1-(hydroxyimino)-$(C_1-C_6)$-alkyl, 1-$[(C_1-C_4)$-alkylimino]-$(C_1-C_4)$-alkyl, 1-$[(C_1-C_4)$-alkoxyimino]-$(C_1-C_6)$-alkyl, $(C_1-C_8)$-alkylcarbonylamino, $(C_2-C_8)$-alkenylcarbonylamino, $(C_2-C_8)$-alkynylcarbonylamino, aminocarbonyl, $(C_1-C_8)$-alkylaminocarbonyl, di-$(C_1-C_6)$-alkylaminocarbonyl, $(C_2-C_6)$-alkenylaminocarbonyl, $(C_2-C_6)$-alkynylaminocarbonyl, $(C_1-C_8)$-alkoxycarbonylamino, $(C_1-C_8)$-alkylaminocarbonylamino, $(C_1-C_6)$-alkylcarbonyloxy which is unsubstituted or substituted by $R^{51}$, or is $(C_2-C_6)$-alkenylcarbonyloxy, $(C_2-C_6)$-alkynylcarbonyloxy, $(C_1-C_8)$-alkylsulfonyl, phenyl, phenyl-$(C_1-C_6)$-alkoxy, phenyl-$(C_1-C_6)$-alkoxycarbonyl, phenoxy, phenoxy-$(C_1-C_6)$-alkoxy, phenoxy-$(C_1-C_6)$-alkoxycarbonyl, phenylcarbonyloxy, phenylcarbonylamino, phenyl-$(C_1-C_6)$-alkylcarbonylamino, the last-mentioned 9 radicals on the phenyl ring being unsubstituted or mono- or polysubstituted, preferably up to trisubstituted, by radicals $R^{52}$; $SiR'_3$, $-OSiR'_3$, $R'_3Si-(C_1-C_8)$-alkoxy, $-CO-O-NR'_2$, $-O-N=CR'_2$, $-N=CR'_2$, $-O-N-R'_2$, $-NR'_2$, $CH(OR')_2$, $-O-(CH_2)_m-CH(OR')_2$, $-CR'''(OR')_2$, $-O-(CH_2)_mCR'''(OR'')_2$ or by $R''O-CHR'''CHCOR''-(C_1-C_6)$-alkoxy, $R^{51}$ is identical or different and is halogen, nitro, $(C_1-C_4)$-alkoxy and phenyl which is unsubstituted or substituted by one or more, preferably up to three, radicals $R^{51}$;

$R^{52}$ is identical or different and is halogen, $(C_1-C_4)$-alkyl, $(C_1-C_4)$-alkoxy, $(C_1-C_4)$-haloalkyl, $(C_1-C_4)$-haloalkoxy or nitro;

R' is identical or different and is hydrogen, $(C_1-C_4)$-alkyl, phenyl which is unsubstituted or substituted by one or more, preferably up to three, radicals $R^{52}$, or two radicals R' together form a $(C_2-C_6)$-alkanediyl chain;

R" is identical or different and is $(C_1-C_4)$-alkyl, or two radicals R" together form a $(C_2-C_6)$-alkanediyl chain;

R'" is hydrogen or $(C_1-C_4)$-alkyl;

w is 0, 1, 2, 3, 4, 5 or 6.

Especially preferred are herbicidal compositions which comprise safeners of the formula (II) and/or (III) wherein the symbols and indices have the following definitions:

$R^{24}$ is hydrogen, $(C_1-C_8)$-alkyl or $(C_3-C_7)$-cycloalkyl, the above carbon-containing radicals being unsubstituted or mono- or polysubstituted by halogen or mono- or disubstituted, by preference monosubstituted, by radicals $R^{50}$, $R^{50}$ is identical or different and is hydroxyl, $(C_1-C_4)$-alkoxy, carboxyl, $(C_1-C_4)$-alkoxycarbonyl, $(C_2-C_6)$-alkenyloxycarbonyl, $(C_2-C_6)$-alkynyloxycarbonyl, 1-(hydroxyimino)-$(C_1-C_4)$-alkyl, 1-[$(C_1-C_4)$-alkylimino]-$(C_1-C_4)$-alkyl and 1-[$(C_1-C_4)$-alkoxyimino]-$(C_1-C_4)$-alkyl; $-SiR'_3$, $-O-N=CR'_2$, $-N=CR'_2$, $-NR'_2$ and $-ONR'_2$ where R' is identical or different and is hydrogen, $(C_1-C_4)$-alkyl or, as a pair, a $(C_4-C_5)$-alkanediyl chain, $R^{27}$, $R^{28}$, $R^{29}$ are identical or different and are hydrogen, $(C_1-C_8)$-alkyl, $(C_1-C_6)$-haloalkyl, $(C_3-C_7)$-cycloalkyl or phenyl which is unsubstituted or substituted by one or more radicals selected from the group consisting of halogen, cyano, nitro, amino, mono- and di-[$(C_1-C_4)$-alkyl]amino, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio and $(C_1-C_4)$-alkylsulfonyl;

$R^{17}$, $R^{19}$ are identical or different and are hydrogen, halogen, methyl, ethyl, methoxy, ethoxy, $(C_1$ or $C_2)$-haloalkyl, by preference hydrogen, halogen or $(C_1$ or $C_2)$-haloalkyl.

Especially preferred are herbicidal compositions comprising safeners of the formula (II) in which the symbols and indices have the following definitions:

$R^{17}$ is hydrogen, halogen, nitro or $(C_1-C_4)$-haloalkyl;

n' is 1, 2 or 3;

$R^{18}$ is a radical of the formula $OR^{24}$;

$R^{24}$ is hydrogen, $(C_1-C_8)$-alkyl or $(C_3-C_7)$-cycloalkyl, where the above carbon-containing radicals are unsubstituted or mono- or polysubstituted, by preference up to trisubstituted, by identical or different halogen radicals or up to disubstituted, by preference monosubstituted, by identical or different radicals selected from the group consisting of hydroxyl, $(C_1-C_4)$-alkoxy, $(C_1-C_4)$-alkoxycarbonyl, $(C_2-C_6)$-alkenyloxycarbonyl, $(C_2-C_6)$-alkynyloxycarbonyl, 1-(hydroxyimino)-$(C_1-C_4)$-alkyl, 1-[$(C_1-C_4)$-alkylimino]-$(C_1-C_4)$-alkyl, 1-[$(C_1-C_4)$-alkoxyimino]-$(C_1-C_4)$-alkyl and radicals of the formulae $-SiR'_3$, $-O-N=R'_2$, $-N=CR'_2$, $-NR'_2$ and $-O-NR'_2$, where the radicals R' in the above-mentioned formulae are identical or different and are hydrogen, $(C_1-C_4)$-alkyl or, as a pair, are $(C_4$ or $C_5)$-alkanediyl;

$R^{27}$, $R^{28}$, $R^{29}$ are identical or different and are hydrogen, $(C_1-C_8)$-alkyl, $(C_1-C_6)$-haloalkyl, $(C_3-C_7)$-cycloalkyl or phenyl which is unsubstituted or substituted by one or more of the radicals selected from the group consisting of halogen, $(C_1-C_4)$-alkyl, $(C_1-C_4)$-alkoxy, nitro, $(C_1-C_4)$-haloalkyl and $(C_1-C_4)$-haloalkoxy.

Also especially preferred are herbicidal compositions comprising safeners of the formula (III) wherein the symbols and indices have the following definitions:

$R^{19}$ is hydrogen, halogen or $(C_1-C_4)$-haloalkyl;

n' is 1, 2 or 3, where $(R^{19})_{n'}$ is by preference 5-Cl;

$R^{20}$ is a radical of the formula $OR^{24}$;

T is $CH_2$ and $R^{24}$ is hydrogen, $(C_1-C_8)$-alkyl, $(C_1-C_8)$-haloalkyl or $(C_1-C_4)$-alkoxy-$(C_1-C_4)$-alkyl, by preference $(C_1-C_8)$-alkyl.

Especially preferred are herbicidal compositions comprising safeners of the formula (II) wherein the symbols and indices have the following definitions:

W is (W1);

$R^{17}$ is hydrogen, halogen or $(C_1-C_2)$-haloalkyl;

n' is 1, 2 or 3, where $(R^{17})_{n'}$ is by preference 2,4-$Cl_2$;

$R^{18}$ is a radical of the formula $OR^{24}$;

$R^{24}$ is hydrogen, $(C_1-C_8)$-alkyl, $(C_1-C_4)$-haloalkyl, $(C_1-C_4)$-hydroxyalkyl, $(C_3-C_7)$-cycloalkyl, $(C_1-C_4)$-alkoxy-$(C_1-C_4)$-alkyl or tri-$(C_1-C_2)$-alkylsilyl, by preference $(C_1-C_4)$-alkyl;

$R^{27}$ is hydrogen, $(C_1-C_8)$-alkyl, $(C_1-C_4)$-haloalkyl or $(C_3-C_7)$-cycloalkyl, by preference hydrogen or $(C_1-C_4)$-alkyl, and $R^{26}$ is hydrogen or $(C_1-C_4)$-alkyl.

Also especially preferred are herbicidal compositions comprising safeners of the formula (II) wherein the symbols and indices have the following definitions:

W is (W2);

$R^{17}$ is hydrogen, halogen or $(C_1-C_2)$-haloalkyl;

n' is 1, 2 or 3, where $(R^{17})_{n'}$ is by preference 2,4-$Cl_2$;

$R^{18}$ is a radical of the formula $OR^{24}$;

$R^{24}$ is hydrogen, $(C_1-C_8)$-alkyl, $(C_1-C_4)$-haloalkyl, $(C_1-C_4)$-hydroxyalkyl, $(C_3-C_7)$-cycloalkyl, $(C_1-C_4$-alkoxy)-$C_1-C_4$-alkyl or tri-$(C_1-C_2)$-alkyl-silyl, by preference $(C_1-C_4)$-alkyl, and $R^{27}$ is hydrogen, $(C_1-C_8)$-alkyl, $(C_1-C_4)$-haloalkyl, $(C_3-C_7)$-cycloalkyl or phenyl, by preference hydrogen or $(C_1-C_4)$-alkyl.

Also especially preferred are herbicidal compositions comprising safeners of the formula (II) wherein the symbols and indices have the following definitions:

W is (W3);

$R^{17}$ is hydrogen, halogen or $(C_1-C_2)$-haloalkyl;

n' is 1, 2 or 3, where $(R^{17})_{n'}$ is by preference 2,4-$Cl_2$;

$R^{18}$ is a radical of the formula $OR^{24}$;

$R^{24}$ is hydrogen, $(C_1-C_8)$-alkyl, $(C_3-C_7)$-cycloalkyl, by preference $(C_1-C_4)$-alkyl, and $R^{28}$ is $(C_1-C_8)$-alkyl or $(C_1-C_4)$-haloalkyl, by preference $C_1$-haloalkyl.

Also especially preferred are herbicidal compositions comprising safeners of the formula (II) wherein the symbols and indices have the following definitions:

W is (W4);

$R^{17}$ is hydrogen, halogen, nitro, $(C_1-C_4)$-alkyl, $(C_1-C_2)$-haloalkyl, by preference $CF_3$;

n' is 1, 2 or 3;

m' is 0 or 1;

$R^{18}$ is a radical of the formula $OR^{24}$;

$R^{24}$ is hydrogen, $(C_1-C_4)$-alkyl, carboxy-$(C_1-C_4)$-alkyl, $(C_1-C_4)$-alkoxycarbonyl-$(C_1-C_4)$-alkyl, by preference ($C_1$–$C_4$)-alkoxy-CO—$CH_2$—, ($C_1$–$C_4$)-alkoxy-CO—C($CH_3$)(H)—, HO—CO—$CH_2$— or HO—CO—C($CH_3$)(H)—, and $R^{29}$ is hydrogen, ($C_1$–$C_4$)-alkyl, ($C_1$–$C_4$)-haloalkyl, ($C_3$–$C_7$)-cycloalkyl or phenyl which is unsubstituted or substituted by one or more of the radicals selected from the group consisting of halogen, ($C_1$–$C_4$)-alkyl, ($C_1$–$C_4$)-haloalkyl, nitro, cyano and ($C_1$–$C_4$)-alkoxy.

The following groups of compounds are especially suitable for use as safeners for the herbicidally active substances of the formula (I):

a) Compounds of the dichlorophenylpyrazoline-3-carboxylic acid type (i.e. of the formula (II) where W=W1 and $(R^{17})_{n'}$=2,4-$Cl_2$), by preference compounds such as ethyl 1-(2,4-dichlorophenyl)-5-(ethoxycarbonyl)-5-methyl-2-pyrazoline-3-carboxylate (II-1), and related compounds as they are described in WO-A 91/07874;

b) dichlorophenylpyrazolecarboxylic acid derivatives (i.e. of the formula (II) where W=(W2) and $(R^{17})_{n'}$=2,4-$Cl_2$), by preference compounds such as ethyl 1-(2,4-dichlorophenyl)-5-methylpyrazole-3-carboxylate (II-2), ethyl 1-(2,4-dichlorophenyl)-5-isopropylpyrazole-3-carboxylate (II-3), ethyl 1-(2,4-dichlorophenyl)-5-(1,1-dimethylethyl)pyrazole-3-carboxylate (II-4), ethyl 1-(2,4-dichlorophenyl)-5-phenylpyrazole-3-carboxylate (II-5) and related compounds as they are described in EP-A-0 333 131 and EP-A-0 269 806.

c) Compounds of the triazolecarboxylic acid type (i.e. of the formula (II) where W=(W3) and $(R^{17})_{n'}$=2,4-$Cl_2$), by preference compounds such as fenchlorazol, i.e. ethyl 1-(2,4-dichlorophenyl)-5-trichloromethyl-(1H)-1,2,4-triazole-3-carboxylate (II-6), and related compounds (see EP-A-0 174 562 and EP-A-0 346 620);

d) compounds of the 5-benzyl- or 5-phenyl-2-isoxazoline-3-carboxylic acid type or the 5,5-diphenyl-2-isoxazoline-3-carboxylic acid type (where W=(W4)), by preference compounds such as ethyl 5-(2,4-dichlorobenzyl)-2-isoxazoline-3-carboxylate (II-7) or ethyl 5-phenyl-2-isoxazoline-3-carboxylate (II-8) and related compounds as they are described in WO-A-91/08202, or ethyl 5,5-diphenyl-2-isoxazoline-3-carboxylate (II-9) or n-propyl 5,5-diphenyl-2-isoxazoline-3-carboxylate (II-10) or ethyl 5-(4-fluorophenyl)-5-phenyl-2-isoxazoline-3-carboxylate (II-11), as they are described in WO-A-95/07897.

e) Compounds of the 8-quinolinoxyacetic acid type, for example those of the formula (III) where $(R^{19})_{n'}$=5-Cl or hydrogen, $R^{20}$=$OR^{24}$ and T=$CH_2$, by preference the compounds 1-methylhexyl (5-chloro-8-quinolinoxy)acetate (III-1, cloquintocet-mexyl), 1,3-dimethylbut-1-yl (5-chloro-8-quinolinoxy)acetate (III-2), 4-allyloxybutyl (5-chloro-8-quinolinoxy)acetate (III-3), 1-allyloxyprop-2-yl (5-chloro-8-quinolinoxy)acetate (III-4), ethyl (5-chloro-8-quinolinoxy)acetate (III-5), methyl (5-chloro-8-quinolinoxy)acetate (III-6), allyl (5-chloro-8-quinolinoxy)acetate (III-7), 2-(2-propylideniminoxy)-1-ethyl (5-chloro-8-quinolinoxy)acetate (III-8), 2-oxoprop-1-yl (5-chloro-8-quinolinoxy)acetate (III-9)

and related compounds as they are described in EP-A-0 860 750, EP-A-0 094 349 and EP-A-0 191 736 or EP-A-0 492 366.

f) Compounds of the (5-chloro-8-quinolinoxy)malonic acid type, i.e. of the formula (III) where $(R^{17})_{n'}$=5-Cl, $R^{20}$=$OR^{24}$, T=—CH(COO-alkyl)-, by preference the compounds diethyl (5-chloro-8-quinolinoxy)malonate, diallyl (5-chloro-8-quinolinoxy)malonate, methyl ethyl (5-chloro-8-quinolinoxy)malonate and related compounds as they are described in EP-A-0 582 198.

g) Compounds of the dichloroacetamide type, i.e. of the formula (IV), by preference:

N,N-diallyl-2,2-dichloroacetamide (dichlormid, from U.S. Pat. No. 4,137,070), 4-dichloroacetyl-3,4-dihydro-3-methyl-2H-1,4-benzoxazine (benoxacor, from EP 0 149 974), N1,N2-diallyl-N-2-dichloroacetylglycinamide (DKA-24, from HU 2143821), 4-dichloroacetyl-1-oxa-4-azaspiro[4,5]decane (AD-67), 2,2-dichloro-N-(1,3-dioxolan-2-ylmethyl)-N-(2-propenyl)acetamide (PPG-1292), 3-dichloroacetyl-2,2,5-trimethyloxazolidine, 3-dichloroacetyl-2,2-dimethyl-5-phenyloxazolidine, 3-dichloroacetyl-2,2-dimethyl-5-(2-thienyl)oxazolidine, 3-dichloroacetyl-5-(2-furanyl)-2,2-dimethyloxazolidine (furilazole, MON 13900), 1-dichloroacetylhexahydro-3,3,8a-trimethylpyrrolo[1,2-a]pyrimidin-6 (2H)-one (dicyclonon, BAS 145138), h) compounds of group B(b), by preference 1,8-naphthalic anhydride, methyl diphenylmethoxyacetate, cyanomethoxyimino(phenyl)acetonitrile (cyometrinil), 1,3-dioxolan-2-ylmethoxyimino(phenyl)acetonitrile (oxabetrinil), 4'-chloro-2,2,2-trifluoroacetophenone O-1,3-dioxolan-2-ylmethyl oxime (fluxofenim), 4,6-dichloro-2-phenylpyrimidine (fenclorim), benzyl 2-chloro-4-trifluoromethyl-1,3-thiazole-5-carboxylate (flurazole), 2-dichloromethyl-2-methyl-1,3-dioxolane (MG-191), N-(4-methylphenyl)-N'-(1-methyl-1-phenylethyl)urea (dymron), 1-[4-(N-2-methoxybenzoylsulfamoyl)phenyl]-3-methylurea, 1-[4-(N-2-methoxybenzoylsulfamoyl)phenyl]-3,3-dimethylurea, 1-[4-(N-4,5-dimethylbenzoylsulfamoyl)phenyl]-3-methylurea, 1-[4-(N-naphthoylsulfamoyl)phenyl]-3,3-dimethylurea, (2,4-dichlorophenoxy)acetic acid (2,4-D), (4-chlorophenoxy)acetic acid, (R,S)-2-(4-chloro-o-tolyloxy)propionic acid (mecoprop), 4-(2,4-dichlorophenoxy)butyric acid (2,4-DB), (4-chloro-o-tolyloxy)acetic acid (MCPA), 4-(4-chloro-o-tolyloxy)butyric acid, 4-(4-chlorophenoxy)butyric acid, 3,6-dichloro-2-methoxybenzoic acid (dicamba), 1-(ethoxycarbonyl)ethyl 3,6-dichloro-2-methoxybenzoate (lactidichlor), and their salts and esters, by preference ($C_1$–$C_8$).

Further preferred safeners are compounds of the formula (V) or salts thereof in which $R^{30}$ is hydrogen, ($C_1$–$C_6$)-alkyl, ($C_3$–$C_6$)-cycloalkyl, where each of the last-mentioned 2 radicals is unsubstituted or substituted by one or more substituents selected from the group consisting of halogen, ($C_1$–$C_4$)-alkoxy, halo- $(C_1-C_6)$-alkoxy and $(C_1-C_4)$-alkylthio and, in the case of cyclic radicals, also $(C_1-C_4)$-alkyl and $(C_1-C_4)$-haloalkyl, $R^{31}$ is hydrogen;

$R^{32}$ is halogen, halo-$(C_1-C_4)$-alkyl, halo-$(C_1-C_4)$-alkoxy, $(C_1-C_4)$-alkyl, $(C_1-C_4)$-alkoxy, $(C_1-C_4)$-alkylsulfonyl, $(C_1-C_4)$-alkoxycarbonyl or $(C_1-C_4)$-alkylcarbonyl, by preference halogen, $(C_1-C_4)$-haloalkyl such as trifluoromethyl, $(C_1-C_4)$-alkoxy, halo-$(C_1-C_4)$-alkoxy, $(C_1-C_4)$-alkoxycarbonyl or $(C_1-C_4)$-alkylsulfonyl, $R^{33}$ is hydrogen;

$R^{34}$ is halogen, $(C_1-C_4)$-alkyl, halo-$(C_1-C_4)$-alkyl, halo-$(C_1-C_4)$-alkoxy, $(C_3-C_6)$-cycloalkyl, phenyl, $(C_1-C_4)$-alkoxy, cyano, $(C_1-C_4)$-alkylthio, $(C_1-C_4)$-alkylsulfinyl, $(C_1-C_4)$-alkylsulfonyl, $(C_1-C_4)$-alkoxycarbonyl or $(C_1-C_4)$-alkylcarbonyl, by preference halogen, $(C_1-C_4)$-alkyl, $(C_1-C_4)$-haloalkyl such as trifluoromethyl, halo-$(C_1-C_4)$-alkoxy, $(C_1-C_4)$-alkoxy or $(C_1-C_4)$-alkylthio, n is 0, 1 or 2 and m is 1 or 2.

Also preferred are safeners of the formula (VI) in which $X^3$ is CH;

$R^{35}$ is hydrogen, $(C_1-C_6)$-alkyl, $(C_3-C_6)$-cycloalkyl, $(C_2-C_6)$-alkenyl, $(C_5-C_6)$-cycloalkenyl, phenyl or 3- to 6-membered heterocyclyl having up to three heteroatoms selected from the group consisting of nitrogen, oxygen and sulfur, the six last-mentioned radicals optionally being substituted by one or more identical or different substituents selected from the group consisting of halogen, $(C_1-C_6)$-alkoxy, $(C_1-C_6)$-haloalkoxy, $(C_1-C_2)$-alkylsulfinyl, $(C_1-C_2)$-alkylsulfonyl, $(C_3-C_6)$-cycloalkyl, $(C_1-C_4)$-alkoxycarbonyl, $(C_1-C_4)$-alkylcarbonyl and phenyl and in the case of cyclic radicals, also $(C_1-C_4)$-alkyl and $(C_1-C_4)$-haloalkyl;

$R^{36}$ is hydrogen, $(C_1-C_6)$-alkyl, $(C_2-C_6)$-alkenyl, $(C_2-C_6)$-alkynyl, the three last-mentioned radicals optionally being substituted by one or more identical or different substituents selected from the group consisting of halogen, hydroxyl, $(C_1-C_4)$-alkyl, $(C_1-C_4)$-alkoxy and $(C_1-C_4)$-alkylthio;

$R^{37}$ is halogen, $(C_1-C_4)$-haloalkyl, $(C_1-C_4)$-haloalkoxy, nitro, $(C_1-C_4)$-alkyl, $(C_1-C_4)$-alkoxy, $(C_1-C_4)$-alkylsulfonyl, $(C_1-C_4)$-alkoxycarbonyl or $(C_1-C_4)$-alkylcarbonyl;

$R^{38}$ is hydrogen;

$R^{39}$ is halogen, nitro, $(C_1-C_4)$-alkyl, $(C_1-C_4)$-haloalkyl, $(C_1-C_4)$-haloalkoxy, $(C_3-C_6)$-cycloalkyl, phenyl, $(C_1-C_4)$-alkoxy, cyano, $(C_1-C_4)$-alkylthio, $(C_1-C_4)$-alkylsulfinyl, $(C_1-C_4)$-alkylsulfonyl, $(C_1-C_4)$-alkoxycarbonyl or $(C_1-C_4)$-alkylcarbonyl;

r is 0, 1 or 2 and q is 1 or 2.

Further particularly preferred safeners are compounds of the formula (VII), in which $R^{40}$ is trifluoromethyl, $R^{41}$ is hydrogen, and $R^{42}$ is hydrogen, methyl or ethyl.

The compounds cited here as safeners (antidotes) reduce or prevent phytotoxic effects which may occur when using the herbicidally active substances of the formula (I) in crops of useful plants without substantially affecting the activity of these herbicidally active substances against weed plants. This allows the field of application of conventional crop protection products to be widened quite considerably and to be extended to, for example, crops such as wheat, barley, corn, and sugar cane in which use of the herbicides was hitherto impossible, or of only limited possibility, that is to say at low rates and with a restricted spectrum.

The herbicidally active substances and the abovementioned safeners can be applied together (as a readymix or by the tank mix method) or in succession in any desired sequence. The weight ratio of safener to herbicidally active substance may vary within wide limits and is preferably within the range from 1:100 to 100:1, in particular from 1:10 to 10:1. The optimum amounts of herbicidally active substance and safener in each case depend on the type of the herbicidally active substance used or on the safener used and on the species of the plant stand to be treated and can be determined in each individual case by simple, routine preliminary experiments.

Main fields of application for the combinations according to the invention are, in particular, corn, sugar cane and cereal crops for example wheat, rye, barley, oats, rice, sorghum, but also cotton and soybeans, preferably sugar cane, cereals, rice and corn.

Depending on their properties, the safeners employed in accordance with the invention can be used for pretreating the seeds of a crop plant (seed dressing), or be incorporated into the seed furrows prior to sowing or applied together with the herbicide before or after plant emergence. The preemergence treatment includes both the treatment of the area under cultivation prior to sowing and the treatment of the areas under cultivation where the seeds have been planted but the plants have not yet emerged. Joint application with the herbicide is preferred. To this end, tank mixes or readymixes can be employed.

The application rates of safener required may vary within wide limits depending on the indication and the herbicidally active substance used and are generally in the range of from 0.001 to 5 kg, preferably 0.005 to 0.5 kg, of active substance per hectare.

The present invention therefore also provides a method of protecting crop plants from phytotoxic side effects of herbicides of the formula (I), which comprises applying an antidote-active amount of a compound of the formula (II), (III), (IV), (V), (VI), (VII) and/or from group (b) to the plants, the seeds of the plants or the area under cultivation, before, after or simultaneously with the herbicidally active substance A of the formula (I).

The herbicide/safener combination according to the invention may also be employed for controlling weed plants in crops of genetically engineered plants which are either known or still to be developed. As a rule, the transgenic plants are distinguished by particular, advantageous properties, for example by resistances to certain crop protection agents, resistances to plant diseases or pathogens causing plant diseases such as particular insects or microorganisms such as fungi, bacteria or viruses. Other particular properties relate, for example, to the harvested material in terms of quantity, quality, storing properties, composition and specific constituents. Thus, transgenic plants are known which have an increased starch content or an altered starch quality, or those where the harvested material has a different fatty acid composition.

The use of the combinations according to the invention is preferred in economically important transgenic crops of useful plants and ornamentals, for example cereals such as wheat, barley, rye, oats, millet, rice, cassaya and corn or else crops of sugar beet, cotton, soya, oilseed rape, potatoes, tomatoes, peas and other types of vegetables.

When the combinations according to the invention are employed in transgenic crops, effects on weed plants to be observed in other crops are frequently accompanied by effects which are specific for application in the transgenic crop in question, for example an altered or specifically widened weed spectrum which can be controlled, altered application rates which may be used, preferably good compatibility with the herbicides to which the transgenic crop is resistant, and altered growth and yield of the transgenic crop plants.

The invention therefore also provides for the use of the combination according to the invention for controlling weed plants in transgenic crop plants.

The safeners of the formulae (III)–(VII) and of group (b) and their combinations with one or more of the abovementioned herbicidally active substances of the formula (I) can be formulated in various ways, depending on the biological and/or chemico-physical parameters specified. Examples of suitable formulations which are possible are: wettable powders (WP), emulsifiable concentrates (EC), water-soluble powders (SP), water-soluble concentrates (SL), concentrated emulsions (BW) such as oil-in-water and water-in-oil emulsions, sprayable solutions or emulsions, capsule suspensions (CS), oil- or water-based dispersions (SC), suspoemulsions, suspension concentrates, dusts (DP), oil-miscible solutions (OL), seed dressing products, granules (GR) in the form of microgranules, spray granules, coated granules and adsorption granules, granules for soil application or broadcasting, water-soluble granules (SG), water-dispersible granules (WG), ULV formulations, microcapsules and waxes.

These individual formulation types are known in principle and described, for example, in: Winnacker-Küchler, "Chemische Technologie" [Chemical Engineering], Volume 7, C. Hauser Verlag Munich, 4$^{th}$ Edition 1986; Wade van Valkenburg, "Pesticide Formulations", Marcel Dekker N.Y., 1973; K. Martens, "Spray Drying Handbook", 3$^{rd}$ Ed. 1979, G. Goodwin Ltd. London.

The formulation auxiliaries which may be required, such as inert materials, surfactants, solvents and other additives are also known and described, for example, in: Watkins, "Handbook of Insecticide Dust Diluents and Carriers", 2$^{nd}$ Ed., Darland Books, Caldwell N.J., H.v. Olphen, "Introduction to Clay Colloid Chemistry", 2$^{nd}$ Ed., J. Wiley & Sons, N.Y.; C. Marsden, "Solvents Guide", 2$^{nd}$ Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active Ethylene Oxide Adducts], Wiss. Verlagsgesell., Stuttgart 1976; Winnacker-Küchler, "Chemische Technologie" [Chemical Engineering], Volume 7, C. Hauser Verlag Munich, 4$^{th}$ Edition 1986.

Based on these formulations, it is also possible to prepare combinations with other substances which act as crop protection agents, such as insecticides, acaricides, herbicides, fungicides, and also with safeners, fertilizers and/or growth regulators, for example in the form of a readymix or as a tank mix.

Wettable powders are preparations which are uniformly dispersible in water and which, besides the active substance, also comprise ionic and/or nonionic surfactants (wetting agents, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate, or else sodium oleoylmethyltaurinate, in addition to a diluent or inert substance. To prepare the wettable powders, the herbicidally active substances are ground finely, for example in customary apparatus such as hammer mills, blower mills and air-jet mills, and they are simultaneously or subsequently mixed with the formulation auxiliaries.

Emulsifiable concentrates are prepared, for example, by dissolving the active substance in an organic solvent such as butanol, cyclohexanone, DMF, or else higher-boiling hydrocarbons such as saturated or unsaturated aliphatics or alicycles, aromatics or mixtures of the organic solvents with the addition of one or more ionic and/or nonionic surfactants (emulsifiers). Examples of substances which can be used as emulsifiers are: calcium alkylarylsulfonates such as calcium dodecylbenzenesulfonate, or nonionic emulsifiers such as fatty acid polyglycol esters, alkylarylpolyglycol ethers, fatty alcohol polyglycol ethers, propylene oxide/ethylene oxide condensates, alkyl polyethers, sorbitan esters, such as sorbitan fatty acid esters or polyoxyethylene sorbitan esters such as polyoxyethylene sorbitan fatty acid esters. Dusts are generally obtained by grinding the active substance with finely divided solid substances, for example talc, natural clays such as kaolin, bentonite and pyrophyllite, or diatomaceous earth.

Suspension concentrates can be water- or oil-based. They can be prepared, for example, by wet-grinding using commercially available bead mills with or without addition of surfactants, for example those which have already been mentioned above in the case of the other formulation types.

Emulsions, for example oil-in-water emulsions (EW), can be prepared, for example, by means of stirrers, colloid mills and/or static mixers using aqueous organic solvents in the presence or absence of surfactants which have already been mentioned above, for example, in the case of the other formulation types.

Granules can be prepared either by spraying the active substance onto adsorptive, granulated inert material or by applying active substance concentrates to the surface of carriers such as sand, kaolinites or granulated inert material with the aid of binders, for example polyvinyl alcohol, sodium polyacrylate or else mineral oils. Suitable active substances can also be granulated in the manner which is conventional for the preparation of fertilizer granules, if desired as a mixture with fertilizers. As a rule, water-dispersible granules are prepared by the customary processes such as spray-drying, fluidized-bed granulation, disk granulation, mixing with high-speed mixers and extrusion without solid inert material.

For the preparation of disk, fluidized-bed, extruder and spray granules see, for example, "Spray-Drying Handbook" 3$^{rd}$ ed. 1979, G. Goodwin Ltd., London; J. E. Browning, "Agglomeration", Chemical and Engineering 1967, pages 147 et seq.; "Perry's Chemical Engineer's Handbook", 5$^{th}$ Ed., McGraw-Hill, New York 1973, p. 8–57.

For further details on the formulation of crop protection products see, for example, G. C. Klingman, "Weed Control as a Science", John Wiley and Sons, Inc., New York, 1961, pages 81–96 and J. D. Freyer, S. A. Evans, "Weed Control Handbook", 5$^{th}$ Ed., Blackwell Scientific Publications, Oxford, 1968, pages 101–103.

As a rule, the agrochemical formulations comprise 0.1 to 99% by weight, in particular 0.1 to 95% by weight, of active substances of the formulae (II)–(VII) and/or (b) or of the herbicide/antidote mixture of active substances (I) and (II) –(VII) and/or (b) and 1 to 99.9% by weight, in particular 5 to 99.8% by weight, of a solid or liquid additive and 0 to 25% by weight, in particular 0.1 to 25% by weight, of a surfactant.

In wettable powders, the active substance concentration is, for example, approximately 10 to 90% by weight, the remainder to 100% by weight being composed of customary formulation components. In the case of emulsifiable concentrates, the active substance concentration is approximately 1 to 80% by weight. Formulations in the form of dusts comprise approximately 1 to 20% by weight of active substances, sprayable solutions approximately 0.2 to 20% by weight of active substances. In the case of granules such as water-dispersible granules, the active substance content depends partly on whether the active compound is in liquid or solid form. The active substance content of the water-dispersible granules is, as a rule, between 10 and 90% by weight.

Besides this, the abovementioned formulations of active substances comprise, if appropriate, the adhesives, wetters, dispersants, emulsifiers, penetrants, preservatives, antifreeze agents, solvents, fillers, carriers, colorants, antifoams, evaporation inhibitors and pH and viscosity regulators which are customary in each case.

Co-components which can be used for the mixtures of herbicides and safeners according to the invention in mixed formulations or in a tank mix are, for example, known active substances as they are described, for example, in Weed Research 26, 441–445 (1986), or "The Pesticide Manual", $10^{th}$ edition, The British Crop Protection Council, 1994, and in the literature cited therein. Herbicides which are known from the literature and which can be combined with the mixtures according to the invention are, for example, the following active substances (note: either the common names in accordance with the International Organization for Standardization (ISO) or the chemical names, if appropriate together with the customary code number, of the compounds are given):

acetochlor; acifluorfen; aclonifen; AKH 7088, i.e. [[[1-[5-[2-chloro-4-(trifluoromethyl)-phenoxy]-2-nitrophenyl]-2-methoxyethylidene]amino]oxy]acetic acid and its methyl ester; alachlor; alloxydim; ametryn; amidosulfuron; amitrol; AMS, i.e. ammonium sulfamate; anilofos; asulam; atrazin; azafenidine (DPX-R6447), azimsulfuron (DPX-A8947); aziprotryn; barban; BAS 516H, i.e. 5-fluoro-2-phenyl-4H-3,1-benzoxazin-4-one; benazolin; benfluralin; benfuresate; bensulfuron-methyl; bensulide; bentazone; benzofluor; benzoylprop-ethyl; benzthiazuron; bialaphos; bifenox; bispyribac-sodium (KIH-2023), bromacil; bromobutide; bromofenoxim; bromoxynil; bromuron; buminafos; busoxinone; butachlor; butamifos; butenachlor; buthidazole; butralin; butroxydim (ICI-0500), butylate; cafenstrole (CH-900); carbetamide; cafentrazone; CDM, i.e. 2-chloro-N,N-di-2-propenylacetamide; CDEC, i.e. 2-chloroallyl diethyldithiocarbamate; chlomethoxyfen; chloramben; chloransulam-methyl (XDE-565), chlorazifop-butyl, chlorbromuron; chlorbufam; chlorfenac; chlorflurecol-methyl; chloridazon; chlorimuron-ethyl; chlornitrofen; chlorotoluron; chloroxuron; chlorpropham; chlorsulfuron; chlorthal-dimethyl; chlorthiamid; cinidon-ethyl, cinmethylin; cinosulfuron; clefoxydim, clethodim; clodinafop and its ester derivatives (for example clodinafop-propargyl); clomazone; clomeprop; cloproxydim; clopyralid; cumyluron (JC 940); cyanazine; cycloate; cyclosulfamuron (AC 014); cycloxydim; cycluron; cyhalofop and its ester derivatives (for example butyl ester, DEH-112); cyperquat; cyprazine; cyprazole; 2,4-DB; dalapon; desmedipham; desmetryn; di-allate; dicamba; dichlobenil; dichlorprop; diclofop and its esters such as diclofop-methyl; diclosulam (XDE-564), diethatyl; difenoxuron; difenoquat; diflufenican; diflufenzopyr-sodium (SAN-835H), dimefuron; dimethachlor; dimethametryn; dimethenamid (SAN-582H); dimethazone, methyl 5-(4,6-dimethylpyrimidin-2-yl-carbamoylsulfamoyl)-1-(2-pyridyl)-pyrazole-4-carboxylate (NC-330); clomazon; dimethipin; dimetrasulfuron, dinitramine; dinoseb; dinoterb; diphenamid; dipropetryn; diquat; dithiopyr; diuron; DNOC; eglinazine-ethyl; EL 177, i.e. 5-Cyano-1-(1,1-dimethylethyl)-N-methyl-1H-pyrazole-4-carboxamide; endothal; epoprodan (MK-243), EPTC; esprocarb; ethalfluralin; ethametsulfuron-methyl; ethidimuron; ethiozin; ethofumesate; F5231, i.e. N-[2-chloro-4-fluoro-5-[4-(3-fluoropropyl)-4,5-dihydro-5-oxo-1H-tetrazol-1-yl]phenyl] ethanesulfonamide; ethoxyfen and its ester (for example ethyl ester, HN-252); ethoxysulfuron (from EP 342569); etobenzanid (HW 52); 3-(4-ethoxy-6-ethyl-1,3,5-triazin-2-yl)-1-(2,3-dihydro-1,1-dioxo-2-methylbenzo[b]thiophene-7-sulfonyl)urea (EP-A 079 683); 3-(4-ethyl-6-methoxy-1,3,5-triazin-2-yl)-1-(2,3-dihydro-1,1-dioxo-2-methylbenzo[b]thiophene-7-sulfonyl)urea (EP-A 079 683); fenoprop; fenoxan, fenoxaprop and fenoxaprop-P and their esters, for example fenoxaprop-P-ethyl and fenoxaprop-ethyl; fenoxydim; fentrazamide (NBA-061); fenuron; flamprop-methyl; flazasulfuron; flufenacet (BAY-FOE-5043), fluazifop and fluazifop-P, florasulam (DE-570) and their esters, for example fluazifop-butyl and fluazifop-P-butyl; fluazolate (Mon-48500), fluchloralin; flucarbazone-sodium; flumetsulam; flumeturon; flumiclorac and its esters (for example pentyl ester, S-23031); flumioxazin (S-482); flumipropyn; flupoxam (KNW-739); fluorodifen; fluoroglycofen-ethyl; flupropacil (UBIC-4243); sodium flupyrsulfuron-methyl (DPX-KE459), fluridone; flurochloridone; fluroxypyr; flurtamone; fluthiacet-methyl (K1H-9201), fomesafen; fosamine; furyloxyfen; glufosinate; glyphosate; halosafen; halosulfuron and its esters (for example methyl ester, NC-319); haloxyfop and its esters; haloxyfop-P (=R-haloxyfop) and its esters; hexazinone; imazamethabenzmethyl; imazamox (AC-299263), imazapyr; imazaquin and salts such as the ammonium salt; imazethamethapyr; imazethapyr; imazosulfuron; iodosulfuron (methyl 4-iodo-2-[3-(4-methoxy-6-methyl-1,3,5-triazin-2-yl) ureidosulfonyl]benzoate, sodium salt, WO 92/13845); ioxynil; isocarbamid; isopropalin; isoproturon; isouron; isoxaben; isoxapyrifop; karbutilate; lactofen; lenacil; linuron; MCPA; MCPB; mecoprop; mefenacet; mefluidid; metamitron; metazachlor; methabenzthiazuron; metham; methazole; methoxyphenone; methyldymron; metabenzuron, methyl 2-[3-(4,6-dimethoxypyrimidin-2-yl) ureidosulfonyl]-4-methanesulfonamidomethylbenzoate (WO 95/10507); methobenzuron; metobromuron; metolachlor; S-metolachlor, metosulam (XRD 511); metoxuron; metribuzin; metsulfuron-methyl; MH; molinate; monalide; monocarbamide dihydrogensulfate; monolinuron; monuron; MT 128, i.e. 6-chloro-N-(3-chloro-2-propenyl)-5-methyl-N-phenyl-3-pyridazinamine; MT 5950, i.e. N-[3-chloro-4-(1-methylethyl)phenyl]-2-methylpentanamide; N,N-dimethyl-2-[3-(4,6-dimethoxypyrimidin-2-yl)ureidosulfonyl]-4-formylaminobenzamide (WO 95/01344); naproanilide; napropamide; naptalam; NC 310, i.e. 4-(2,4-dichlorobenzoyl)-1-methyl-5-benzyloxypyrazole; neburon; nicosulfuron; nipyraclofen; nitralin; nitrofen; nitrofluorfen; norflurazon; orbencarb; oryzalin; oxadiargyl (RP-020630); oxadiazon; oxaziclomefone (MY-100), oxyfluorfen; oxasulfuron (CGA-277476), paraquat; pebulate; pendimethalin; pentoxazone (KPP-314), perfluidone; phenisopham; phenmedipham; picloram; piperophos; piributicarb; pirifenopbutyl; pretilachlor; primisulfuron-methyl; pracarbazone-sodium; procyazine; prodiamine; profluralin; proglinazine-ethyl; prometon; prometryn; propachlor; propanil; propaquizafop and its esters; propazine; propham; propisochlor; propyzamide; prosulfalin; prosulfocarb; prosulfuron (CGA-152005); prynachlor; pyraflufen-ethyl (ET-751), pyrazon; pyrazosulfuron-ethyl; pyrazoxyfen; pyribenzoxim, pyridafol; pyridate; pyriminobac-methyl (KIH-6127), pyrithiobac (KIH-2031); pyroxofop and its esters (for example propargyl ester); quinclorac; quinmerac; quinofop and its ester derivatives, quizalofop and quizalofop-P and their ester derivatives, for example quizalofop-ethyl; quizalofop-P-tefuryl and -ethyl; renriduron; rimsulfuron (DPX-E 9636); S 275, i.e. 2-[4-chloro-2-fluoro-5-(2-propynyloxy)-phenyl]-4,5,6,7-tetrahydro -2H-indazole; secbumeton; sethoxydim; siduron; simazine; simetryn; SN 106279, i.e. 2-[[7-[2-chloro-4-(trifluoromethyl)phenoxy]-2-naphthalenyl]oxy]propanoic acid and its methyl ester; sulfentrazon (FMC-97285, F-6285); sulfazuron; sulfometuron-methyl; sulfosate (ICI-A0224); sulfosulfuron (MON-37500), TCA; tebutam (GCP-5544); tebuthiuron; tepraloxydim (BAS-620H), terbacil; terbucarb; terbuchlor; terbumeton; terbuthylazine; terbutryn; TFH 450, i.e. N,N-diethyl-3-[(2-ethyl-6-methylphenyl)sulfonyl]-1H-1,2,4-triazole-1-carboxamide; thenylchlor (NSK-850); thiazaflu-ron; thiazopyr (Mon-13200); thidiazimin (SN-124085); thifensulfuron-methyl; thiobencarb; thiocarbazil; tralkoxy-dim; tri-allate; triasulfuron; triaziflam (DH-1105); triazofe-namide; tribenuron-methyl; triclopyr; tridiphane; trietazine; trifluralin; triflusulfuron and esters (for example methyl ester, DPX-66037); trimeturon; tsitodef; vernolate; WL 110547, i.e. 5-phenoxy-1-[3-(trifluoromethyl)phenyl]-1H-tetrazole; UBH-509; D-489; LS 82-556; KPP-300; KPP-421, MT-146, NC-324; KH-218; DPX-N8189; DOWCO-535; DK-8910; V-53482; PP-600; MBH-001.

For use, the formulations which are in commercially available form are, if desired, diluted in the customary manner, for example using water in the case of wettable powders, emulsifiable concentrates, dispersions and water-dispersible granules. Preparations in the form of dusts, soil granules, granules for broadcasting and sprayable solutions are usually not diluted any further with other inert substances prior to use.

The necessary application rate of the herbicides of the formula (I) varies with the external conditions such as, inter alia, temperature, humidity, and the nature of the herbicide used. It may be varied within wide limits, for example between 0.001 and 10.0 kg/ha or more of active substance, but it is preferably between 0.005 and 5 kg/ha.

The examples which follow serve to illustrate the invention:

A. Formulation Examples a) A dust is obtained by mixing 10 parts by weight of a compound of the formula (II)–(VII) and/or from group (b) or of an active substance mixture of a herbicidally active substance of the formula (I) and a safener of the formula (II)–(VII) and/or from group (b) and 90 parts by weight of talc as inert substance and comminuting the mixture in a hammer mill.

b) A wettable powder which is readily dispersible in water is obtained by mixing 25 parts by weight of a compound of the formula (II), (III), (IV) and/or from group (b) or of an active substance mixture of a herbicidally active substance of the formula (I) and a safener of the formula (II), (III), (IV) and/or from group (b), 64 parts by weight of kaolin-containing quartz as inert substance, 10 parts by weight of potassium lignosulfonate and 1 part by weight of sodium oleoylmethyltaurinate as wetter and dispersant, and grinding the mixture in a pinned-disk mill.

c) A dispersion concentrate which is readily dispersible in water is obtained by mixing 20 parts by weight of a compound of the formula (II)–(VII) and/or from group (b) or of an active substance mixture of a herbicidally active substance of the formula (I) and a safener of the formula (II)–(VII) and/or from group (b), 6 parts by weight of alkylphenol polyglycol ether (®Triton X 207), 3 parts by weight of isotridecanol polyglycol ether (8 EO) and 71 parts by weight of paraffinic mineral oil (boiling range, for example, approx. 255 to above 277° C.) and grinding the mixture in a ball mill to a fineness of below 5 microns.

d) An emulsifiable concentrate is obtained from 15 parts by weight of a compound of the formula (II)–(VII) and/or from group (b) or of an active substance mixture of a herbicidally active substance of the formula (I) and a safener of the formula (II)–(VII) and/or from group (b), 75 parts by weight of cyclohexanone as solvent and 10 parts by weight of ethoxylated nonylphenol as emulsifier.

e) Water-dispersible granules are obtained by mixing
   75 parts by weight of a compound of the formula (II)–(VII) and/or from group (b) or of an active substance mixture of a herbicidally active substance of the formula (I) and a safener of the formula (II)–(VII) and/or from group (b)
   10 parts by weight of calcium lignosulfonate,
   5 parts by weight of sodium lauryl sulfate,
   3 parts by weight of polyvinyl alcohol and
   7 parts by weight of kaolin,
   grinding the mixture on a pinned-disk mill and granulating the powder in a fluidized bed by spraying on water as granulation liquid.

f) Water-dispersible granules are also obtained by homogenizing and precomminuting, in a colloid mill,
   25 part(s) by weight of a compound of the formula (II)–(VII) and/or from groups (b) or of an active substance mixture of a herbicidally active substance of the formula (I) and a safener of the formula (II)–(VII) and/or from group (b)
   5 part(s) by weight of sodium 2,2'-dinaphthylmethane-6,6'-disulfonate
   2 part(s) by weight of sodium oleoylmethyltaurinate,
   1 part(s) by weight of polyvinyl alcohol,
   17 part(s) by weight of calcium carbonate and
   50 part(s) by weight of water,
   subsequently grinding the mixture on a bead mill and atomizing and drying the resulting suspension in a spray tower by means of a single-substance nozzle.

BIOLOGICAL EXAMPLES

1. Damage Scoring

The damage to the plants is evaluated visually in comparison with control plants, according to a scale from 0–100%:

0%=no perceptible action in comparison with the untreated plant,

100%=treated plant dies.

2. Herbicide Action and Safener Action Preemergence

Seeds of monocotyledonous and dicotyledonous broad-leaf weed plants and of crop plants are placed in sandy loam and plastic pots of 9 cm in diameter and are covered with soil. Alternatively, for the test under conditions for paddy rice, broadleaf weeds which occur in rice growing are cultivated in waterlog soil, the amount of water introduced into the pots being such that the water comes up to the soil surface or several millimeters above it. The herbicide/safener active substance combinations of the invention, formulated in the form of emulsifiable concentrates, and, in parallel trials, the correspondingly formulated individual active substances, are then applied to the surface of the covering earth or, in the case of rice, poured into the irrigation water in the form of emulsions, at a water application rate of 300 l/ha (converted), at different concentrations.

Following treatment, the pots are placed in a greenhouse and are kept under good growth conditions. Visual scoring of the plant and/or emergence damage takes place after the trial plants have emerged, after a trial period of 3–4 weeks, in comparison to untreated controls. As the trials show, the herbicidal compositions of the invention have a good preemergence herbicidal action against a broad spectrum of gramineous and broadleaf weeds, with substantial reduction—that is, from around 50% up to 100% less herbicide damage—in damage to crop plants such as corn, rice, wheat or barley or other cereals in comparison with the use of the individual herbicides without safeners.

3. Herbicide Action and Safener Action Postemergence

Seeds of monocotyledonous and dicotyledenous broadleaf weed plants and of crop plants are placed in sandy loam and plastic pots, colored with soil and grown in a greenhouse under good growth conditions. Alternatively, for the test under conditions for paddy rice, broadleaf weeds that occur in rice growing, and rice, are cultivated in pots in which water stands up to 2 cm above the soil surface, and are cultivated during the growth phase. About three weeks after sowing, the trial plants are treated at the three-leaf stage. The herbicide/safener active substance combinations of the invention, formulated as emulsifable or concentrates, and, in parallel trials, the correspondingly formulated individual active substances are sprayed on the green parts of the plants at different concentrations with a water application rate of 300 l/ha (converted) and, after the trial plants have stood in the greenhouse for 3 weeks under optimum growth conditions, the action of the preparations is scored visually in comparison with untreated controls. In the case of rice or broadleaf weeds which occur in rice growing, the active substances are also introduced directly into the irrigation water (application in analogy to granular application, as it is known) or on plants and sprayed into the irrigation water. In the case of field trials, seeds of monocotyledonous and dicotyledonous broadleaf weed plants and of crop plants were placed in sandy loam, covered with earth and grown. Further treatment was as described above. Evaluation in the case took place two weeks after the treatment with herbicide and/or safener. In the case of the trials with sugar cane, evaluation was carried out after 63 days. The experiments show that the herbicidal compositions of the invention exhibit a good postemergence herbicidal action against a broad spectrum of gramineous and broadleaf weeds, with substantial reduction—i.e., around 50% up to 100% less herbicide damage—in damage to crop plants such as sugar cane, corn, rice, wheat or barley or other cereals in comparison with the use of the individual herbicides without safeners.

Table 1 specifies the herbicides used, and table 2 the safeners. Tables 3 to 7 indicate the percentage by which the damage in corn, sugar cane, rice, wheat or barley, respectively, caused by a herbicide is lessened by simultaneous use of the safener.

TABLE 1

Herbicides

| No. | Structure |
|---|---|
| H1 | 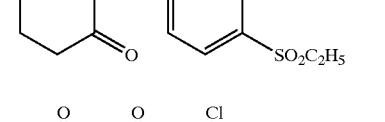 |
| H2 | 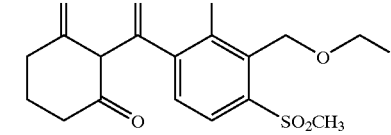 |
| H3 | 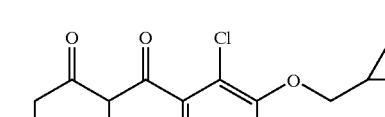 |
| H4 | 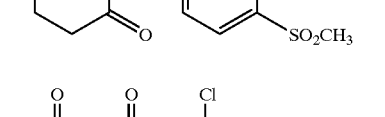 |
| H5 | 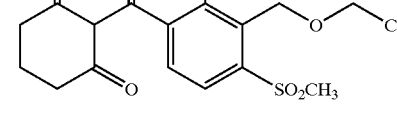 |
| H6 | 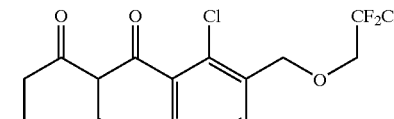 |
| H7 | 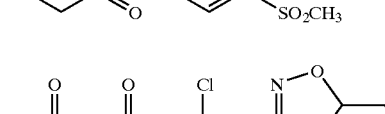 |
| H8 | 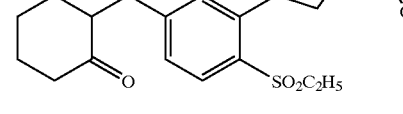 |

TABLE 2

Safeners

| No. | Structure |
|---|---|
| S1 | ethyl 5,5-diphenyl-4,5-dihydroisoxazole-3-carboxylate |
| S2 | 3-(dichloroacetyl)-5-(2-furyl)-2,2-dimethyl-1,3-oxazolidine |
| S3 | 1-(4-chlorophenyl)-2,2,2-trifluoro-1-[(1,3-dioxolan-2-ylmethoxy)imino]ethane |
| S4 | 1-methylhexyl (5-chloroquinolin-8-yloxy)acetate |
| S5 | diethyl 1-(2,4-dichlorophenyl)-5-methyl-4,5-dihydro-1H-pyrazole-3,5-dicarboxylate |
| S6 | (Z)-2-fluoro-3-[4-(trifluoromethyl)phenyl]acrylic acid |
| S7 | N-cyclopropyl-4-[({[(2-methoxybenzoyl)amino]sulfonyl})]benzamide |
| S8 | 2-methoxy-N-({[4-(2-methoxyacetamido)phenyl]sulfonyl})benzamide |
| S9 | 5,5-diphenyl-4,5-dihydroisoxazole-3-carboxylic acid |
| S10 | 2-methoxy-N-({[4-(3-methylureido)phenyl]sulfonyl})benzamide |

TABLE 3

Postemergence field trials, corn

| Compound No. | | Rate [g/ha] | | | Reduction in damage to |
|---|---|---|---|---|---|
| Herbicide | Safener | Herbicide | | Safener | corn from using safener |
| H1 | S1 | 200 | + | 200 | 54% |
| H1 | S7 | 400 | + | 100 | 50% |
| H2 | S1 | 100 | + | 100 | 100% |
| H2 | S1 | 200 | + | 100 | 96% |
| H2 | S7 | 80 | + | 80 | 100% |
| H2 | S8 | 80 | + | 80 | 100% |
| H2 | S9 | 80 | + | 80 | 100% |
| H2 | S10 | 80 | + | 80 | 100% |
| H3 | S1 | 150 | + | 150 | 84% |
| H4 | S1 | 150 | + | 150 | 89% |
| H5 | S1 | 150 | + | 150 | 100% |
| H6 | S1 | 150 | + | 150 | 100% |
| H7 | S1 | 150 | + | 150 | 100% |
| H8 | S1 | 150 | + | 150 | 83% |

TABLE 4

Postemergence field trials, sugar cane

| Compound No. | | Rate [g/ha] | | | Reduction in damage to sugar cane |
|---|---|---|---|---|---|
| Herbicide | Safener | Herbicide | | Safener | from using safener |
| H2 | S1 | 200 | + | 200 | 60% |

TABLE 5

Postemergence greenhouse trials, rice

| Compound No. | | Rate [g/ha] | | | Reduction in damage to rice |
|---|---|---|---|---|---|
| Herbicide | Safener | Herbicide | | Safener | from using safener |
| H1 | S1 | 100 | + | 200 | 78% |
| H1 | S3 | 120 | + | 600 | 68% |
| H2 | S2 | 200 | + | 600 | 63% |
| H8 | S1 | 200 | + | 200 | 71% |

TABLE 6

Postemergence greenhouse trials, wheat

| Compound No. | | Rate [g/ha] | | Reduction in damage to wheat from using safener |
|---|---|---|---|---|
| Herbicide | Safener | Herbicide | Safener | |
| H1 | S4 | 20 | + 80 | 21% |
| H1 | S5 | 20 | + 80 | 29% |
| H2 | S4 | 100 | + 100 | 60% |
| H2 | S5 | 20 | + 20 | 71% |
| H2 | S5 | 100 | + 100 | 70% |
| H2 | S6 | 60 | + 60 | 50% |

TABLE 7

Postemergence greenhouse trials, barley

| Compound No. | | Rate [g/ha] | | Reduction in damage to barley from using safener |
|---|---|---|---|---|
| Herbicide | Safener | Herbicide | Safener | |
| H2 | S5 | 180 | + 180 | 100% |
| H2 | S5 | 100 | + 100 | 100% |
| H2 | S6 | 20 | + 80 | 75% |

In table 8, following the working examples, the seed was first treated with safener and, after sowing and emergence, the plant was then treated with herbicide. Here again, a marked reduction in the damage caused by the herbicide is evident in comparison to the seed which was not treated with safener. The amount of safener indicated is based on the amount of seed.

TABLE 8

Postemergence greenhouse trials following seed treatment, corn

| Compound No. | | Rate [g/ha] | Rate [g/ha] | Reduction in damage to corn from using safener |
|---|---|---|---|---|
| Herbicide | Safener | Herbicide | Safener | |
| H2 | S9 | 80 | 0.05 | 87% |
| H2 | S3 | 80 | 0.1 | 84% |
| H2 | S7 | 80 | 0.01 | 84% |
| H2 | S8 | 80 | 0.05 | 87% |

What is claimed is:

1. A herbicidal composition comprising:
A) a herbicidally effective amount of one or more compounds of the formula (I)

$$(R^4)_b \text{—[cyclohexanedione ring with } R^3\text{]—C(=O)—[phenyl with } (R^1)_a \text{ and } R^2\text{]} \qquad (I)$$

in which the symbols and indices have the following definitions:

$R^1$ is nitro, amino, halogen, cyano, $(C_1-C_4)$-alkyl, $(C_2-C_4)$-alkenyl, $(C_2-C_4)$-alkynyl, $(C_1-C_4)$-haloalkyl, $(C_2-C_4)$-haloalkenyl, $(C_2-C_4)$-haloalkynyl, $(C_1-C_4)$-haloalkoxy, $(C_1-C_4)$-haloalkylthio, $(C_1-C_4)$-alkoxycarbonyl, $(C_1-C_4)$-alkylsulfonyl, $(C_1-C_4)$-alkylsulfinyl, $(C_1-C_4)$-alkylthio, $(C_1-C_4)$-alkoxy, $(C_1-C_4)$-alkoxy-$(C_1-C_4)$-alkoxy, $(C_1-C_4)$-alkylcarbonyl, $(C_1-C_4)$-alkylaminosulfonyl, $(C_1-C_4)$-dialkylaminosulfonyl, $(C_1-C_4)$-alkylcarbamoyl, $(C_1-C_4)$-dialkylcarbamoyl, $(C_1-C_4)$-alkoxy-$(C_1-C_4)$-alkyl, $(C_1-C_4)$-alkylamino or $(C_1-C_4)$-dialkylamino;

$R^2$ is $(C_1-C_4)$-haloalkoxy-$(C_1-C_4)$-alkyl, $(C_1-C_4)$-alkoxy-$(C_1-C_4)$-alkoxy-$(C_1-C_4)$-alkoxy-$(C_1-C_4)$-alkyl, $(C_3-C_6)$-cycloalkoxy-$(C_1-C_4)$-alkyl, $(C_3-C_6)$-cycloalkyl-$(C_1-C_4)$-alkoxy, tetrahydrofuran-2-yl-methoxy-$(C_1-C_4)$-alkyl, tetrahydrofuran-3-yl-methoxy-$(C_1-C_4)$-alkyl or a heterocyclic radical from the group consisting of isoxazol-3-yl and 4,5-dihydroisoxazol-3-yl which is substituted by a radical from the group consisting of cyanomethyl, ethoxymethyl and methoxymethyl;

$R^3$ is $OR^5$, cyano, halogen, cyanato, thiocyanato, $(C_1-C_4)$-alkylthio, $(C_1-C_4)$-alkylsulfinyl, $(C_1-C_4)$-alkylsulfonyl, $(C_2-C_4)$-alkenylthio, $(C_2-C_4)$-alkenylsulfinyl, $(C_2-C_4)$-alkenylsulfonyl, $(C_2-C_4)$-alkynylthio, $(C_2-C_4)$-alkynylsulfinyl, $(C_2-C_4)$-alkynylsulfonyl, $(C_1-C_4)$-haloalkylthio, $(C_2-C_4)$-haloalkenylthio, $(C_2-C_4)$-haloalkynylthio, $(C_1-C_4)$-haloalkylsulfinyl, $(C_2-C_4)$-haloalkenylsulfinyl, $(C_2-C_4)$-haloalkynylsulfinyl, $(C_1-C_4)$-haloalkylsulfonyl, $(C_2-C_4)$-haloalkenylsulfonyl or $(C_2-C_4)$-haloalkynylsulfonyl;

$R^4$ is $(C_1-C_4)$-alkyl;

$R^5$ is hydrogen, $(C_1-C_4)$-alkyl, $(C_1-C_4)$-haloalkyl or $(C_1-C_4)$-alkoxy-$(C_1-C_4)$-alkyl;

a is 0, 1, 2 or 3;

b is 0, 1 or 2; and

B) an antidote-active amount of one or more compounds of the formula $$(R^{17})_{n'}\text{—[phenyl]—W—C(=O)—}R^{18} \qquad (II)$$

in which the symbols and indices have the following definitions:

n' is a natural number from 1 to 5,

W is a radical $$\text{—}(CH_2)_{m'}\text{—[isoxazoline with } R^{29}\text{]} \qquad (W4)$$

m' is 0 or 1;

$R^{17}$ is are identical or different and are hydrogen, halogen, $(C_1-C_4)$-alkyl, $(C_1-C_4)$-alkoxy, nitro or $(C_1-C_4)$-haloalkyl;

$R^{18}$ is are identical or different and are $OR^{24}$, $SR^{24}$ or $NR^{24}R^{25}$ or a saturated or unsaturated 3- to 7-membered heterocycle containing at least one nitrogen atom and up to 3 heteroatoms which is bonded by the nitrogen atom to the carbonyl group in (II) or (III) and is unsubstituted or substituted by radicals from the group consisting of $(C_1-C_4)$-alkyl, $(C_1-C_4)$-alkoxy and unsubstituted or substituted phenyl;

$R^{24}$ is hydrogen or an unsubstituted or substituted aliphatic hydrocarbon radical;

$R^{25}$ is hydrogen, $(C_1-C_6)$-alkyl, $(C_1-C_6)$-alkoxy or substituted or unsubstituted phenyl; and $R^{29}$ is identical or different and are hydrogen, $(C_1-C_8)$-alkyl, $(C_1C_6)$-haloalkyl, $(C_3-C_{12})$-cycloalkyl or substituted or unsubstituted phenyl;

inclusive of the stereoisomers and the agriculturally customary salts.

2. The herbicidal composition as claimed in claim 1, comprising compounds of the formula (I) wherein the symbols and indices have the following definitions:

$R^1$ is nitro, cyano, chlorine, fluorine, methyl, trifluoromethyl, methylsulfonyl or ethylsulfonyl;

$R^2$ is pentafluoroethoxymethyl, 2,2-difluoroethoxymethyl, 2,2,2-trifluoroethoxymethyl, 2,2,3,3-tetrafluoropropoxymethyl, cyclopentyloxymethyl, cyclohexyloxymethyl, cyclopropyloxy, tetrahydrofuran-2-ylmethoxymethyl, methoxyethoxyethoxymethyl, or 4,5-dihydroisoxazol-3-yl which is substituted by a radical from the group consisting of cyanomethyl, ethoxymethyl and methoxymethyl;

$R^3$ is $OR^5$;

$R^5$ is hydrogen;

a is 2;

b is 0, and the two radicals $R^1$ are in positions 2 and 4 of the phenyl ring.

3. The herbicidal composition as claimed in claim 1, wherein the ratio of herbicide to safener is from 1:10 to 10:1.

4. The herbicidal composition as claimed in claim 1, comprising a further herbicide.

5. The herbicidal composition as claimed in claim 1 wherein component B is ethyl 5,5-diphenyl-2-isoxazoline-3-carboxylate.

6. The herbicidal composition as claimed in claim 1 wherein component B is of formula (II) and W is W4, and wherein component A is

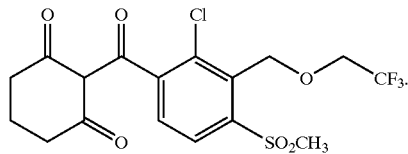

7. The herbicidal composition as claimed in claim 1 wherein component B is ethyl 5,5-diphenyl-2-isoxazoline-3-carboxylate, and wherein component A is

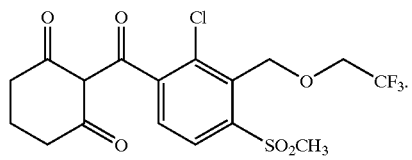

8. The herbicidal composition as claimed in claim 1, wherein $R^{24}$ is hydrogen, $(C_1-C_8)$-alkyl, $(C_3-C_{12})$-cycloalkyl, $(C_2-C_8)$-alkenyl and $(C_2-C_{18})$-alkynyl, where the carbon-containing groups can be substituted by one or more radicals $R^{50}$;

$R^{50}$ is identical or different and is halogen, hydroxyl, $(C_1-C_8)$-alkoxy, $(C_1-C_8)$-alkylthio, $(C_2-C_8)$-alkenylthio, $(C_2-C_8)$-alkynylthio, $(C_{2}-C_{48})$-alkenyloxy, $(C_2-C_8)$-alkynyloxy, $(C_3-C_7)$-cycloalkyl, $(C_3-C_7)$-cycloalkoxy, cyano, mono- and di-$(C_1-C_4)$-alkyl)amino, carboxyl, $(C_1-C_8)$-alkoxycarbonyl, $(C_2-C_8)$-alkenyloxycarbonyl, $(C_1-C_8)$-alkylthiocarbonyl, $(C_2-C_8)$-alkynyloxycarbonyl, $(C_1-C_8)$-alkylcarbonyl, $(C_2-C_8)$-alkenylcarbonyl, $(C_2-C_8)$-alkynylcarbonyl, 1-(hydroxyimino)-$(C_1-C_6)$ alkyl, 1-[$(C_1-C_4)$-alkylimino]-$(C_1-C_4)$-alkyl, 1-[$(C_1-C_4)$-alkoxyimino]-$(C_1-C_6)$-alkyl, $(C_1-C_8)$-alkylcarbonylamino, $(C_2-C_8)$-alkenylcarbonylamino, $(C_2-C_8)$-alkynylcarbonylamino, aminocarbonyl, $(C_1-C_8)$-alkylaminocarbonyl, di-$(C_1-C_6)$-alkylaminocarbonyl; $(C_2-C_6)$-alkenylaninocarbonyl, $(C_2-C_6)$-alkynylaminocarbonyl, $(C_1-C_8)$-alkoxycarbonylamino, $(C_1-C_8)$-alkylaminocarbonylamino, $(C_1-C_6)$-alkylcarbonyloxy which is unsubstituted or substituted by $R^{51}$, or is $(C_2-C_6)$-alkenylcarbonyloxy, $(C_2-C_6)$-alkynylcarbonyloxy, $(C_1-C_8)$-alkylsulfonyl, phenyl, phenyl-$(C_1-C_6)$-alkoxy, phenyl-$(C_1-C_6)$ alkoxycarbonyl, phenoxy, phenoxy-$(C_1-C_6)$-alkoxy, phenoxy-$(C_1-C_6)$alkoxycarbonyl, phenylcarbonyloxy, phenylcarbonylamino, phenyl-$(C_1-C_6)$ alkylcarbonylamino, for the phenyl ring being the last-mentioned 9 radicals unsubstituted or mono- or polysubstituted by radicals $R^{52}$; $SiR'_3$, $OSiR'_3$, $R'_3Si$-(($C_1-C_8$)-alkoxy, —CO—O—NR'$_2$, —O—N=CR'$_2$, —N=CR'$_2$, —O—NR'$_2$, —NR'$_2$, —CH(OR')$_2$, —O—(CH$_2$)$_m$—CH(OR')$_2$, —CR'''(OR')$_2$, —O—(CH$_2$)$_m$CR'''(OR'')$_2$ or by R''O—CHR'''CHCOR''—$(C_1-C_6)$-alkoxy, $R^{51}$ is identical or different and is halogen, nitro, $(C_1-C_4)$-alkoxy and phenyl which is unsubstituted or substituted by one or more radicals $R^{51}$, $R^{52}$ is identical or different and is halogen, $(C_1-C_4)$-alkyl, $(C_1-C_4)$-alkoxy, $(C_1-C_4)$-haloalkyl, $(C_1-C_4)$-haloalkoxy or nitro;

R' is identical or different and is hydrogen, $(C_1-C_4)$-alkyl, phenyl which is unsubstituted or substituted by one or more radicals $R^{52}$, or two radicals R' together form a $(C_2-C_6)$-alkanediyl chain;

R'' is identical or different and is $(C_1-C_4)$-alkyl, or two radicals R'' together form a $(C_2-C_6)$-alkanediyl chain;

R''' is hydrogen or $(C_1-C_4)$-alkyl;

m is 0, 1, 2, 3, 4, 5 or 6.

9. The herbicidal composition as claimed in claim 8, wherein $R^{24}$ is hydrogen, $(C_1-C_8)$-alkyl or $(C_3-C_7)$-cycloalkyl, the above carbon-containing radicals being unsubstituted or mono- or polysubstituted by halogen or mono or disubstitutedby radicals $R^{50}$, $R^{50}$ is identical or different and is hydroxyl, $(C_1-C_4)$-alkoxy, carboxyl, $(C_1-C_4)$-alkoxycarbonyl, $(C_2-C_6)$-alkenyloxycarbonyl, $(C_2-C_6)$-alkynyloxycarbonyl, 1-(hydroxyimino)-$(C_1-C_4)$-alkyl, 1-[$(C_1-C_4)$-alkylimino]-$(C_1-C_4)$-alkyl and 1-[$(C_1-C_4)$-alkoxyimino]-$(C_1-C_4$-alkyl; —SiR'$_3$, —O—N=CR'$_2$, —N=CR'$_2$, —NR'$_2$ and ONR'$_2$ where R' is identical or different and is hydrogen, $(C_1-C_4)$-alkyl or, as a pair, a $(C_4-C_5)$-alkanediyl chain, $R^{29}$ is identical or different and are hydrogen, $(C_1-C_8)$-alkyl, $(C_1-C_6)$-haloalkyl, $(C_3-C_7)$-cycloalkyl or phenyl which is unsubstituted or substituted by one or more radicals selected from the group consisting of halogen, cyano, nitro, amino, mono- and di-[$(C_1-C_4$-alkyl] amino, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio and $(C_1-C_4)$alkylsulfonyl;

$R^{17}$ is identical or different and are hydrogen, halogen, methyl, ethyl, methoxy, ethoxy, or ($C_1$ or $C_2$).

10. The herbicidal composition as claimed in claim 1, wherein $R^{17}$ is halogen, nitro or ($C_1$–$C_4$)-haloalkyl;

$R^{18}$ is a radical of the formula $OR^{24}$;

$R^{24}$ is hydrogen, ($C_1$–$C_8$)-alkyl or ($C_3$–$C_7$)-cycloalkyl, where the above carbon-containing radicals are unsubstituted or mono- or polysubstiftutedby identical or different halogen radicals or up to disubstituted by identical or different radicals selected from the group consisting of hydroxyl, ($C_1$–$C_4$)-alkoxy, ($C_1$–$C_4$)-alkoxycarbonyl, ($C_2$–$C_6$)-alkenyloxycarbonyl, ($C_2$–$C_6$)-alkynyloxycarbonyl, 1-(hydroxyimino)-($C_1$–$C_4$)-alkyl, 1-[($C_1$–$C_4$)-alkylimino]-($C_1$–$C_4$)-alkyl, 1-[($C_1$–$C_4$)-alkoxymino]-($C_1$–$C_4$)-alkyl and radicals of the formulae —$SiR'_3$, —O—N=$R'_2$, —N=$CR'_2$, —$NR'_2$ and —O—$NR'_2$, where the radicals R' in the abovementioned formulae are identical or different and are hydrogen, ($C_1$–$C_4$)-alkyl or, as a pair, are ($C_4$ or $C_5$)-alkanediyl;

$R^{29}$ is identical or different and are hydrogen, ($C_1$–$C_8$)-alkyl, ($C_1$–$C_6$)-haloalkyl, ($C_3$–$C_7$)-cycloalkyl or phenyl which is unsubstituted or substituted by one or more of the radicals selected from the group consisting of halogen, ($C_1$–$C_4$)-alkyl, ($C_1$–$C_4$)-alkoxy, nitro, ($C_1$–$C_4$)-haloalkyl and ($C_1$–$C_4$)-haloalkoxy.

11. A method of controlling weed plants in crops which comprises applying a herbicidally active amount of a herbicidal composition as claimed in claim 1 to the weed plants, plants, seeds of plants, or the area on which the plants are growing.

12. The method as claimed in claim 11, wherein the plants are from the group consisting of sugar cane, corn, wheat, rye, barley, oats, rice, sorghum, cotton, and soya.

13. The method as claimed in claim 11, wherein the plants have been genetically modified.

* * * * *